(12) United States Patent
Warmke et al.

(10) Patent No.: US 6,358,701 B1
(45) Date of Patent: Mar. 19, 2002

(54) **DNA MOLECULES ENCODING *CTENOCEPHALIDES FELIS* GLUTAMATE GATED CHLORIDE CHANNELS**

(75) Inventors: Jeffrey W. Warmke, Edison; Doris F. Cully, Scotch Plains, both of NJ (US); Adrian Etter, Villars SurGlane (SE); Philip S. Paress, Maplewood, NJ (US); Charles J. Cohen, Warren, NJ (US); Richard Brochu, Gillette, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/130,339

(22) Filed: Aug. 6, 1998

Related U.S. Application Data

(60) Provisional application No. 60/055,451, filed on Aug. 11, 1997.

(51) Int. Cl.$^7$ .................. C07H 21/04; C12N 15/12; C12N 15/63
(52) U.S. Cl. .................. 435/69.1; 435/320.1; 435/325; 435/252.3; 435/172.3; 536/23.1; 536/24.31
(58) Field of Search .................. 435/69.1, 320.1, 435/325, 252.3, 172.3; 536/23.1, 24.31

(56) References Cited

U.S. PATENT DOCUMENTS

| | | | |
|---|---|---|---|
| 5,385,831 A | 1/1995 | Mulvhill et al. | 435/69.1 |
| 5,527,703 A | 6/1996 | Cully et al. | 435/252.3 |
| 5,693,492 A | * 12/1997 | Cully et al. | 435/69.1 |

FOREIGN PATENT DOCUMENTS

| | | |
|---|---|---|
| WO | WO92/22652 | 12/1992 |
| WO | WO93/07161 | 4/1993 |
| WO | WO95/32302 | 11/1995 |
| WO | WO96/34940 | 11/1996 |

OTHER PUBLICATIONS

Arena et al., 'Avermectin–Sensitive Chloride Currents Induced by Caenorhabditis elegans RNA in Xenopus Oocytes'; Molecular Pharm. vol. 40, pp. 368–374 (1991).
Zufall et al., 'The Insecticide Avermectin B1a Activates a Chloride Channel in Crayfish Muscle Membrane'; Jour. of Exper. Biol. vol. 142, pp. 191–205 (1989).
Rohrer 'Photoaffinity labeling of avermectin binding sites from Caenorhabditis elegans and Drosophila melanogaster', Proc Natl. Acad. Sci., vol. 89, pp. 4168–4172 May 1992.
Lea et al., 'The Site of Action of Iboteni Acid and teh letification of Two Populations of Glutamate Receptors on Insect Muscle–Fibres', Comp. Gen. Pharmacol. 4: pp. 333–350 (1973).
Lingle et al., 'A glutamate–activated chloride conductance on a crustacean muscle', Brain Research 212: pp. 481–488 (1981).
Cull–Candy, 'Two Types of Extrajunctonal L–Glutamate Receptors in Locust Muscle Fibres', J. Physiol. 255: pp. 449–464 (1976).

Cully et al., 'Identification of a Drosophila melanogaster Glutamate–gated Chloride Channel Sensitive to the Antiparasitic Agent Avermectin ', J. Biol. Chem. 271: pp. 20187–20191 (1996).
Horseman et al., 'The effects of L–glutamate on cultered insect neurone', Neuroscience Letters, 85, pp. 65–70 (1988).
Wafford et al., 'L–Glutamate Receptors on the Cell Body Membrane of an Identified Insect Motor Neurone', J. Exp. Biol. 144, pp. 449–462 (1989).
Cully et al. 'Cloning of an avermectin–sensitive glutamate–gated chloride channel from Caenorhabditis elegans'; Nature, vol. 371, pp. 707–711, (1994).
Ffrench–Constant et al., "Molecular cloning and transformation of cyclodiene resistance in Drosophila: An invertebrate –aminobutyric acid subtype A receptor locus"; Proc. Natl. Acad. Sci. USA, vol. 88, pp. 7209–7213 (1991).
Ffrench–Constant et al., 'A point mutation in a Drosophila GABA receptor confers insecticide resistance', Nature vol. 363, pp. 449–451 (1993).
Harlow et al., 'Antibodies, A Laboratory Manual' Published by Cold Spring Harbor Laboratory Press NY, pp. 93–115 (Jan. 1988).
Harvey et al., "Sequence of a functional invertebrate GABA–a receptor Subunit which can form a chimeric receptor with a vertebrate alpha subunit", The EMBO Jour. vol. 10, No. 11 pp. 3239–3245 (1991).
Henderson et al., 'Characterization of a Putative –Aminobutyric Acid (Gaba) Receptor Beta subunit gene from Drosophila melanogaster'; Biochem. and Biophysical Res. Comm. vol. 193, No. 2, pp. 474–482 (1993).

(List continued on next page.)

*Primary Examiner*—Elizabeth Kemmerer
*Assistant Examiner*—Nirmal S. Basi
(74) *Attorney, Agent, or Firm*—Sheldon O. Heber; Jack L. Tribble

(57) ABSTRACT

To date, L-glutamate-gated chloride (GluCl) channels have been observed only in invertebrate organisms. Modulators of this channel (either agonists or antagoinists) will interfere with neurotransmission. For example, agents such as avermectins activate the GluCl, causing paralysis due to blocking of neurotranmitter release, resulting in death of the organism. Because GluCl channels are invertebreate specific, they are excellent targets for the discovery of novel insecticides, anthelminths and parasiticides that will display a marked safety profile because of the lack of mechanism based toxicity in vertebrate organisms. The present specification discloses isolation of a cDNA clone from the cat flea *Ctenocephalides felis* (CfGluCl-1) that encodes a L-glutamate-gated chloride channel. Heterologous expression of CfGluCl-1 cRNA in *Xenopus oocytes* results in robust expression of a L-glutamate-gated chloride current and the channel is activated and potentiated by avermectins. The expression of CfGluCl-1 in a heterologous expression system if useful to screens for novel GluCl channel agonsts and antagonsits. Additionally, this specification disclose impoved methods of screening for GluCl channel modulators.

24 Claims, 8 Drawing Sheets

OTHER PUBLICATIONS

Hollman et al., 'Cloning by functional expression of a member of the glutamate receptor family', Nature, vol. 342, pp. 643–648 (1989).

Hutton et al. 'A novel invertebrate GABA–a receptor–like polypeptide', FEBS 12670, vol. 326, No. 1,2,3, pp. 112–116 (1993).

Julius et al., 'Molecular Characterization of a Functional cDNA Encoding the Serotonin 1c Receptor '; Science, vol. 241, pp. 558–564 (1988).

Masood et al., 'Differential Ethanol Sensitivity of Recombinant N–Methyl–D–aspartate Receptor Subunits'; Mol. Pharmacol., vol. 45 pp. 324–329 (1994).

Thompson et al., 'Cloning and sequencing of the cylcodiene insecticide resistance gene from the yellow fever mosquito Aedes aegypti'; FEBS 12616, vol. 325, No. 3, 187–190 (1993).

Ultsch et al., 'Glutamate receptors of Drosophila melanogaster'; FEBS 12573, vol. 324 (2) pp. 171–177 (1993).

Zaman et al., 'Unusual effects of benzodiazepines and cyclodiene insecticides on an expressed invertebrate GABA –a receptor', FEBS 11356, vol. 307, No. 3, 351–354 (1992).

* cited by examiner

```
  1 ATGGACAGCA TTAGTTTGCT CCTACTTTTG ATAACATGTC TAAGTCTACA
 51 CACATGCTTA TCTGCAAATG CAAAACCTCG TCTAGGAGGC GGCAAAGAAA
101 ATTTCAGGGC CAAAGAAAAG CAAGTTCTGG ACCAAATTTT AGGCCCAGGC
151 CATTACGATG CCAGAATAAG GCCTTCTGGA GTCAATGGAA CTGGAGACGG
201 TCCGACCGTG GTAGCAGTCA ACATCTATCT GAGATCAATC AGCGAAATAG
251 ATGACTACAA AATGGAATAC AGTGTCCAGT TAACTTTCAG GGAACAATGG
301 CAGGATGAGA GGTTGAAATT TAACGACTTT GGAGGTCGTT TAAAATACTT
351 AACACTAACC GAAGCAAGTC GTGTATGGAT GCCCGATTTG TTCTTTGCGA
401 ATGAAAAGGA GGGCCACTTT CACAACATCA TCATGCCGAA CGTCTACATT
451 CGTATTTTTC CTTACGGTTC CGTACTATAC AGCATCAGGA TATCGCTTAC
501 TTTGGCGTGT CCTATGAATC TGAAACTGTA TCCGCTCGAT AGGCAGGTGT
551 GCTCTCTCCG GATGGCCAGT TATGGTTGGA CCACAAACGA TCTGGTGTTT
601 TTGTGGAAGG AAGGTGACCC GGTGCAGGTT GTCAAGAATC TACATCTGCC
651 CAGGTTTACG TTGGAGAAGT TCTTGACGGA TTATTGTAAC AGCAAAACCA
701 ATACCGGTGA ATACAGTTGC CTGAAGGTCG ACCTGCTCTT TAAACGAGAG
751 TTCTCGTACT ACCTGATCCA GATCTACATT CCTTGTTGCA TGTTGGTGAT
801 CGTTTCCTGG GTGTCGTTCT GGTTGGACCA GGGAGCGGTT CCGGCCAGAG
851 TATCACTGGG TGTGACCACT CTCCTCACCA TGGCCACCCA GACGTCGGGC
901 ATAAACGCCT CCCTGCCGCC AGTGTCCTAC ACAAAAGCCA TCGACGTCTG
```

FIG.1A

```
 951 GACCGGAGTC TGCCTCACGT TCGTCTTCGG GGCTTTGCTC GAATTCGCCC
1001 TCGTCAACTA CGCCTCCAGA TCCGATATGC ACAGGGAAAA CATGAAGAAA
1051 AAGCGCAGGG AACTTGAACA AGCAGCCAGC CTGGACGCCG CCTCCGACCT
1101 GATGGACGGC ACTGATGGCA CTTTTGCTAT GAAGCCTCTG GTACGCCACT
1151 CCGTCGACGC CGTCGGTCTC GATAAGGTTC GTCAGTGCGA GATACACATG
1201 CAGCCGGCGT CCAGGCAGAA CTGCTGCAGG AGCTGGATAA GCAAATTCCC
1251 GACGAGGTCG AAACGCATCG ACGTCATATC AAGAATCACT TTCCCGCTGG
1301 TGTTTGCTTT GTTCAATCTG GTGTACTGGT CGACCTATTT GTTCAGGGAC
1351 GAGGCGGAGG AGAATTAG
```

FIG.1B

```
  1 MDSISLLLLL ITCLSLHTCL SANAKPRLGG GKENFRAKEK QVLDQILGPG
 51 HYDARIRPSG VNGTGDGPTV VAVNIYLRSI SEIDDYKMEY SVQLTFREQW
101 QDERLKFNDF GGRLKYLTLT EASRVWMPDL FFANEKEGHF HNIIMPNVYI
151 RIFPYGSVLY SIRISLTLAC PMNLKLYPLD RQVCSLRMAS YGWTTNDLVF
201 LWKEGDPVQV VKNLHLPRFT LEKFLTDYCN SKTNTGEYSC LKVDLLFKRE
251 FSYYLIQIYI PCCMLVIVSW VSFWLDQGAV PARVSLGVTT LLTMATQTSG
301 INASLPPVSY TKAIDVWTGV CLTFVFGALL EFALVNYASR SDMHRENMKK
351 KRRELEQAAS LDAASDLMDG TDGTFAMKPL VRHSVDAVGL DKVRQCEIHM
401 QPASRQNCCR SWISKFPTRS KRIDVISRIT FPLVFALFNL VYWSTYLFRD
451 EAEEN
```

FIG.2

```
  1 ATGGACAGCA TTAGTTTGCT CCTACTTTTG ATAACATGTC TAAGTCTACA
 51 CACATGCTTA TCTGCAAATG CAAAACCTCG TCTAGGAGGC GGCAAAGAAA
101 ATTTCAGGGC CAAAGAAAAG CAAGTTCTGG ACCAAATTTT AGGCCCAGGC
151 CATTACGATG CCAGAATAAG GCCTTCTGGA GTCAATGGAA CTGGAATACA
201 GTGTCCAGTT AACTTTCAGG GAACAATGGC AGGATGAGAG GTTGAAATTT
251 AACGACTTTG GAGGTCGTTT AAAATACTTA ACACTAACCG AAGCAAGTCG
301 TGTATGGATG CCCGATTTGT TCTTTGCGAA TGAAAAGGAG GGCCACTTTC
351 ACAACATCAT CATGCCGAAC GTCTACATTC GTATTTTTCC TTACGGTTCC
401 GTACTATACA GCATCAGGAT ATCGCTTACT TTGGCGTGTC CTATGAATCT
451 GAAACTGTAT CCGCTCGATA GGCAGGTGTG CTCTCTCCGG ATGGCCAGTT
501 ATGGTTGGAC CACAAACGAT CTGGTGTTTT TGTGGAAGGA AGGTGACCCG
551 GTGCAGGTTG TCAAGAATCT ACATCTGCCC AGGTTTACGT TGGAGAAGTT
601 CTTGACGGAT TATTGTAACA GCAAAACCAA TACCGGTGAA TACAGTTGCC
651 TGAAGGTCGA CCTGCTCTTT AAACGAGAGT TCTCGTACTA CCTGATCCAG
701 ATCTACATTC CTTGTTGCAT GTTGGTGATC GTTTCCTGGG TGTCGTTCTG
751 GTTGGACCAG GGAGCGGTTC CGGCCAGAGT ATCACTGGGT GTGACCACTC
801 TCCTCACCAT GGCCACCCAG ACGTCGGGCA TAAACGCCTC CCTGCCGCCA
851 GTGTCCTACA CAAAAGCCAT CGACGTCTGG ACCGGAGTCT GCCTCACGTT
901 CGTCTTCGGG GCTTTGCTCG AATTCGCCCT CGTCAACTAC GCCTCCAGAT
```

FIG.3A

```
 951 CCGATATGCA CAGGGAAAAC ATGAAGAAAA AGCGCAGGGA ACTTGAACAA
1001 GCAGCCAGCC TGGACGCCGC CTCCGACCTG ATGGACGGCA CTGATGGCAC
1051 TTTTGCTATG AAGCCTCTGG TACGCCACTC CGTCGACGCC GTCGGTCTCG
1101 ATAAGGTTCG TCAGTGCGAG ATACACATGC AGCCGGCGTC CAGGCAGAAC
1151 TGCTGCAGGA GCTGGATAAG CAAATTCCCG ACGAGGTCGA AACGCATCGA
1201 CGTCATATCA AGAATCACTT TCCCGCTGGT GTTTGCTTTG TTCAATCTGG
1251 TGTACTGGTC GACCTATTTG TTCAGGGACG AGGCGGAGGA GAATTAG
```

FIG.3B

```
 1 MDSISLLLLL ITCLSLHTCL SANAKPRLGG GKENFRAKEK QVLDQILGPG
51 HYDARIRPSG VNGTGIQCPV NFQGTMAG
```

FIG.4

DNA MOLECULES ENCODING *CTENOCEPHALIDES FELIS* GLUTAMATE GATED CHLORIDE CHANNELS

CROSS REFERENCE TO RELATED APPLICATIONS

This is a continuation of provisional application number 60/055,451 filed Aug. 11, 1997.

STATEMENT REGARDING FEDERALLY-SPONSORED R&D

Not applicable.

REFERENCE TO MICROFICHE APPENDIX

Not applicable.

FIELD OF THE INVENTION

The present invention relates in part to isolated nucleic acid molecules (polynucleotides) which encode *Ctenocephalides felis* (flea) glutamate gated chloride channels. The present invention also relates to recombinant vectors and recombinant hosts which contain a DNA fragment encoding *C. felis* glutamate gated chloride channels, substantially purified forms of associated *C. felis* glutamate gated chloride channels, associated mutant proteins, and methods associated with identifying compounds which modulate associated *Ctenocephalides felis* glutamate gated chloride channels, which will be useful as insecticides.

BACKGROUND OF THE INVENTION

Glutamate-gated chloride channels, or H-receptors, have been identified in arthropod nerve and muscle (Lingle et al, 1981, Brain Res. 212: 481–488; Horseman et al., 1988, Neurosci. Lett. 85: 65–70; Wafford and Sattelle, 1989, J. Exp. Bio. 144:449–462; Lea and Usherwood, 1973, Comp. Gen. Parmacol. 4: 333–350; and Cull-Candy, 1976, J. Physiol. 255:449–464).

Additionally, glutamate-gated chloride channels have been cloned from the soil nematode *Caenorhabditis elegans* (Cully et al., 1994, Nature 371: 707–711; see also U.S. Pat. No. 5,527,703) and *Drosophila melanogaster* (Cully et al., 1996, J. Biol. Chem. 271: 20187–20191).

Invertebrate glutamate-gated chloride channels are important targets for the widely used avermectin class of anthelmintic and insecticidal compounds. The avermectins are a family of macrocyclic lactones originally isolated from the actinomycete *Streptomyces avermitilis*. The semisynthetic avermectin derivative, ivermectin (22,23-dihydro-avermectin $B_{1a}$), is used throughout the world to treat parasitic helminths and insect pests of man and animals. The avermectins remain the most potent broad spectrum endectocides exhibiting low toxicity to the host. After many years of use in the field, there remains little resistance to avermectin in the insect population. The combination of good therapeutic index and low resistance strongly suggests that the glutamate-gated chloride (GluCl) channels remain good targets for insecticide development.

It would be advantageous to identify additional invertebrate genes encoding encoding GluCl channels in order to allow screening to identify novel GluCl channel modulators that may have insecticidal, mitacidal and/or nematocidal activity for animal health or crop protection. The present invention addresses and meets these needs by disclosing isolated nucleic acid molecules which express a *Ctenocephalides felis* GluGl channel wherein expression of flea GluCl cRNA in *Xenopus oocytes* results in an active GluCl channel.

SUMMARY OF THE INVENTION

The present invention relates to isolated nucleic acid molecules (polynucleotides) which encode novel invertebrate GluCl channel proteins, especially nucleic acid molecules which encode a functional *C. felis* GluCl (herein, "CfGluCl") channel.

The present invention also relates to isolated nucleic acid fragments of CfGluCl which encode mRNA expressing a biologically active CfGluCl channel. Any such polynucleotide includes but is not necessarily limited to nucleotide substitutions, deletions, additions, amino-terminal truncations and carboxy-terminal truncations such that these mutations encode cRNA which express a functional *C. felis* GluCl channel in a eukaryotic cell, such as Xenopus oocytes, so as to be useful for screening for agonists and/or antagonists of *C. felis* GluCl activity.

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA), including but not limited to messenger RNA (mRNA) encoding a biologically active *C. felis* GluCl channel and complementary RNA (cRNA) transcribed from a recombinant expression vector comprising a DNA molecule which encodes a full-length or biologically active portion of the full-length *C. felis* GluCl channel.

A preferred aspect of the present invention is disclosed in FIGS. 1A–B and SEQ ID NO:1, an isolated cDNA molecule encoding a *C. felis* GluCl channel, CfGluCl-1.

The present invention relates to recombinant vectors and recombinant hosts, both prokaryotic and eukaryotic, which contain the substantially purified nucleic acid molecules disclosed throughout this specification, especially a nucleic acid molecule encoding a *C. felis* GluCl channel, CfGluCl, such as the cDNA molecule disclosed in FIGS. 1A–B and set forth in SEQ ID NO:1.

The present invention also relates to a substantially purified form of a *C. felis* GluCl channel protein and especially the *C. felis* GluCl channel disclosed in FIG. 2 and set forth in SEQ ID NO:2.

The present invention relates to a substantially purified membrane preparation which comprises a *C. felis* GluCl channel and is essentially free from contaminating proteins, including but not limited to other *C. felis* source proteins or host proteins from a recombinant cell which expresses CfGluCl. Especially preferred is a membrane preparation which comprises *C. felis* GluCl channel disclosed in FIG. 2 and set forth in SEQ ID NO:2. To this end, the present invention also relates to a substantially purified membrane preparation which is purified from a recombinant host, whether a recombinant eukaryotic or recombinant prokaryotic host, wherein a recombinant vector expresses a *C. felis* GluCl channel. Especially preferred is a membrane preparation which comprises a recombinant form of the *C. felis* GluCl channel, CfGluCl, disclosed in FIG. 2 and set forth in SEQ ID NO:2, referred to as CfGluCl-1.

The present invention also relates to biologically active fragments and/or mutants of a *C. felis* GluCl channel protein, including but not limited to the CfGluCl protein disclosed in FIG. 2 and set forth in SEQ ID NO:2, including but not necessarily limited to amino acid substitutions, deletions, additions, amino terminal truncations and carboxy-terminal truncations such that these mutations provide for a biologically active channel which is useful in screening for agonists and/or antagonists of C. felis GluCl channel activity.

The present invention also relates to an isolated nucleic acid molecule (polynucleotide) which encodes a truncated form of the flea GluCl channel protein (herein, "tr-CfGluCl"), as exemplified in FIG. 3 and set forth in SEQ ID NO:3. Co-expression of tr-CfGluCl in *Xenopus oocytes* with CfGluCl is shown to inhibit glutamate-gated channel activity.

The present invention also relates to isolated nucleic acid fragments of tr-CfGluCl-1 (SEQ ID NO:3) which encodes cRNA expressing a biologically active form of tr-CfGluCl, including but not limited to inhibition or promotion of CfGluCl channel activity in the target cell type. Any such polynucleotide includes but is not necessarily limited to nucleotide substitutions, deletions, additions, amino-terminal truncations and carboxy-terminal truncations from the truncated form.

Again, any such truncated nucleic acid molecule (as compared to CfGluCl) may include a deoxyribonucleic acid molecule (DNA), such as genomic DNA and complementary DNA (cDNA), which may be single (coding or non-coding strand) or double stranded, as well as synthetic DNA, such as a synthesized, single stranded polynucleotide. The isolated nucleic acid molecule of the present invention may also include a ribonucleic acid molecule (RNA), including but not limited to messenger RNA (mRNA) or complementary RNA (cRNA) transcribed from a recombinant expression vector comprising a DNA molecule which encodes a truncated version of the full-length C. felis GluCl channel.

A preferred aspect of this portion of the invention is disclosed in FIGS. 3A–B and SEQ ID NO:4, an isolated cDNA molecule encoding a truncated version of the C. felis GluCl channel.

The present invention also relates to recombinant vectors and recombinant hosts, both prokaryotic and eukaryotic, which contain the substantially purified nucleic acid molecules disclosed throughout this specification, especially a nucleic acid molecule encoding a truncated version of a C. felis GluCl channel such as the cDNA molecule disclosed in FIGS. 3A–B and set forth in SEQ ID NO:3.

The present invention also relates to a substantially purified form of a truncated version of the C. felis GluCl channel, trCfGluCl, and especially the truncated version of the C. felis GluCl channel, which is disclosed in FIG. 4 and as set forth in SEQ ID NO:4, referred to as trCfGluCl-1.

The present invention also relates to biologically active fragments and/or mutants of the truncated C. felis GluCl channel, trCfGluCl-1, including but not necessarily limited to amino acid substitutions, deletions, additions, amino terminal truncations and carboxy-terminal truncations.

It is an object of the present invention to provide an isolated nucleic acid molecule which encodes a novel form of a C. felis GluCl channel and biologically active fragments thereof which are derivatives of SEQ ID NO:2.

It is a further object of the present invention to provide the C. felis GluCl channel proteins or protein fragments encoded by the nucleic acid molecules referred to in the preceding paragraph.

It is a further object of the present invention to provide recombinant vectors and recombinant host cells which comprise a nucleic acid sequence encoding a C. felis GluCl channel or a biological equivalent thereof.

It is an object of the present invention to provide a substantially purified form of a C. felis GluCl channel or a biological equivalent thereof, as set forth in SEQ ID NO:2.

It is also an object of the present invention to provide a membrane preparation membrane preparation which comprises a C. felis GluCl channel and is essentially free from contaminating proteins. This membrane preparation includes, but is not limited to, a membrane preparation purified from a recombinant host.

It is an object of the present invention to provide for biologically active fragments and/or mutants of CfGluCl, including but not necessarily limited to amino acid substitutions, deletions, additions, amino terminal truncations and carboxy-terminal truncations such that these mutations provide for proteins or protein fragments of diagnostic, therapeutic or prophylactic use.

It is an object of the present invention to provide a substantially purified form of CfGluCl-1, as set forth in SEQ ID NO:4.

It is an object of the present invention to provide for biologically active fragments and/or mutants of CfGluCl, including but not necessarily limited to amino acid substitutions, deletions, additions, amino terminal truncations and carboxy-terminal truncations.

As used herein, "GluCl" refers to a glutamate-gated chloride channel.

As used herein, "CfGluCl" refers to a biologically active form of a C. felis glutamate-gated chloride channel.

As used herein, "cDNA" refers to complementary DNA.

As used herein, "mRNA" refers to messenger RNA.

As used herein, "cRNA" refers to complementary RNA, transcribed from a recombinant cDNA template.

BRIEF DESCRIPTION OF THE DRAWINGS

FIGS. 1A–B shows the nucleotide sequence which comprises the open reading frame encoding the C. felis GluCl channel, CfGluCl-1 (SEQ ID NO:1).

FIG. 2 shows the amino acid sequence of CfGluCl-1 (SEQ ID NO:2).

FIGS. 3A–B shows the nucleotide sequence which comprises the open reading frame encoding the truncated C. felis GluCl channel, trCfGluCl-1 (SEQ ID NO:3).

FIG. 4 shows the amino acid sequence of trCfGluCl-1 (SEQ ID NO:4).

FIG. 5A shows superimposed current recordings in response to 10, 30, 100 and 300 $\mu$M glutamate. FIG. 5B shows the concentration-response curve for glutamate.

FIG. 7A shows superimposed current recordings showing activation by 100 $\mu$M glutamate and 10 nM IVM-PO$_4$. FIG. 7B shows the concentration-response curve for IVM-PO$_4$ for CfGluCl (0 mV), DmGluCl (0 mV) and DmGluCl (−80 mV).

DETAILED DESCRIPTION OF THE INVENTION

Figure 5A:
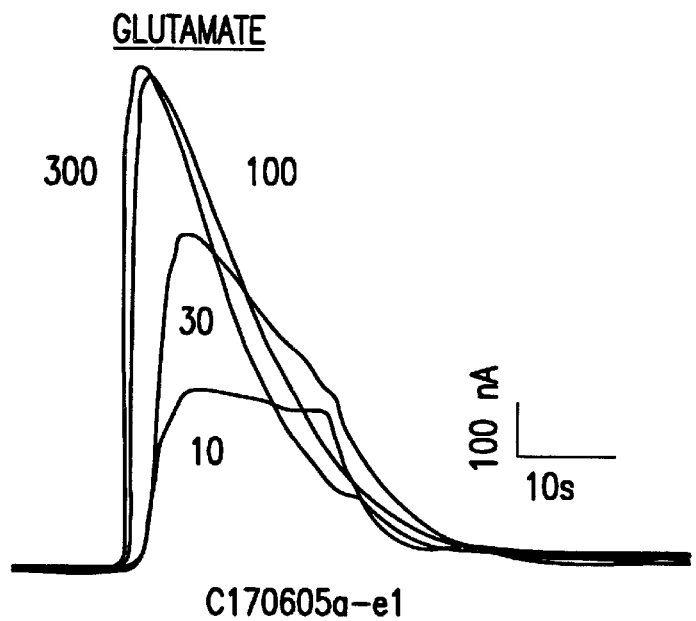
FIGS. 5A and 5B show activation of CfGluCl-1 by glutamate.

L-glutamate-gated chloride (GluCl) channels have been observed only in invertebrate organisms. A modulator of this channel (either an agonist or antagonist) will interfere with neurotransmission. Agents such as avermectins activate this channel and cause paralysis due to block of neurotranmitter release, resulting in death of the organism. Because GluCl channels are invertebrate specific, they are excellent targets for the discovery of novel insecticides, anthelminthics and parasiticides that will display a marked safety profile because of the lack of mechanism based toxicity in vertebrate organisms. The present invention relates to isolated nucleic acid molecules (polynucleotides) which encode novel invertebrate GluCl channel proteins, especially nucleic acid molecules which encode a functional *C. felis* GluCl channel (herein, "CfGluCl"). Heterologous expression of CfGluCl cRNA in *Xenopus oocytes* results in robust expression of a L-glutamate-gated chloride current. The CfGluCl channel is activated and potentiated by avermectins (e.g., ivermectin phosphate). The expression of CfGluCl-1 in a heterologous expression system can be used to establish screens for novel GluCl channel modulators. Such compounds will be useful as antiparasitics and insecticides in human and animal health and crop protection, because they will be devoid of mechanism based vertebrate toxicity.

To this end, the present invention also relates to isolated nucleic acid fragments of CfGluCl which encode cRNA expressing a biologically CfGluCl channel. Any such polynucleotide includes but is not necessarily limited to nucleotide substitutions, deletions, additions, amino-terminal truncations and carboxy-terminal truncations such that these mutations encode cRNA which express a functional *C. felis* GluCl channel in a eukaryotic cell, such as Xenopus oocytes, so as to be useful for screening for agonists and/or antagonists of *C. felis* GluCl activity.

A preferred aspect of the present invention is disclosed in FIGS. 1A–B and SEQ ID NO:1, an isolated cDNA molecule encoding a *C. felis* GluCl channel, CfGluCl-1.

The present invention also relates to recombinant vectors and recombinant hosts, both prokaryotic and eukaryotic, which contain the substantially purified nucleic acid molecules disclosed throughout this specification, especially a nucleic acid molecule encoding a *C. felis* GluCl channel, CfGluCl, such as the cDNA molecule disclosed in FIGS. 1A–B and set forth in SEQ ID NO:1.

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA), including but not limited to messenger RNA (mRNA) encoding a biologically active *C. felis* GluCl channel and complementary RNA (cRNA) transcribed from a recombinant expression vector comprising a DNA molecule which encodes a full-length or biologically active portions of the full-length *C. felis* GluCl channel.

It is known that there is a substantial amount of redundancy in the various codons which code for specific amino acids. Therefore, this invention is also directed to those DNA sequences transcribing mRNA or cRNA comprising alternative codons which encode an identical amino acid, as shown below:
A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, ULTUU
G=Gly=Glycine: codons GGA, GGC, GGG, GGU
H=His=Histidine: codons CAC, CAU
I=Ele=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site-directed mutagenesis. Examples of altered properties include but are not limited to changes in the affinity of an enzyme for a substrate or a receptor for a ligand.

As used herein, "purified" and "isolated" are utilized interchangeably to stand for the proposition that the nucleic acid, protein, or respective fragment thereof in question has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in pure quantities so as to afford the opportunity to generate polyclonal antibodies, monoclonal antibodies, amino acid sequencing, and peptide digestion. Therefore, the nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods while a chemically synthesized nucleic acid sequence is considered to be substantially purified when purified from its chemical precursors.

The present invention also relates to a substantially purified form of a *C. felis* GluCl channel, CfGluCl, and especially the *C. felis* GluCl channel which is disclosed in FIG. 2 and as set forth in SEQ ID NO:2, referred to as CfGluCl-1.

The present invention also relates to a substantially purified membrane preparation which comprises a *C. felis* GluCl channel and is essentially free from contaminating proteins. Especially preferred is a membrane preparation which comprises a *C. felis* GluCl channel disclosed in FIG. 2 and set forth in SEQ ID NO:2, referred to as CfGluCl-1.

The present invention also relates to a substantially purified membrane preparation which is purified from a recombinant host, whether a recombinant eukaryotic or recombinant prokaryotic host, wherein a recombinant vector expresses a C. felis GluCl channel. Especially preferred is a membrane preparation which comprises a recombinant form of the C. felis GluCl channel, CfGluCl, disclosed in FIG. 2 and set forth in SEQ ID NO:2, referred to as CfGluCl-1.

The present invention also relates to biologically active fragments and/or mutants of CfGluCl-1, including but not necessarily limited to amino acid substitutions, deletions, additions, amino terminal truncations and carboxy-terminal truncations such that these mutations provide for a biologically active channel which is useful in screening for agonists and/or antagonists of C. felis GluCl channel activity.

As used herein, a "biologically active equivalent" or "functional derivative" of a wild-type C. felis GluCl channel possesses a biological activity that is substantially similar to the biological activity of the wild type C. felis GluCl channel. The term "functional derivative" is intended to include the "fragments," "mutants," "variants," "degenerate variants," "analogs" and "homologues" or to "chemical derivatives" of the wild type C. felis GluCl channel protein. The term "fragment" is meant to refer to any polypeptide subset of a wild-type C. felis GluCl channel. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the C. felis GluCl channel and/or C. felis GluCl channel derivative. The term "variant" is meant to refer to a molecule substantially similar in structure and function to either the entire wild-type protein or to a fragment thereof. A molecule is "substantially similar" to a wild-type C. felis GluCl channel and/or C. felis GluCl channel-like protein if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the full-length C. felis GluCl channel and/or C. felis GluCl channel or to a biologically active fragment thereof.

The present invention also relates to isolated an isolated nucleic acid molecule (polynucleotide) which encodes a truncated form of the flea GluCl channel protein (herein, "tr-CfGluCl"), as exemplified in FIGS. 3A–B and SEQ ID NO:3. Co-expression of tr-CfGluCl in Xenopus oocytes with CfGluCl inhibits glutamate-gated channel activity.

The present invention also relates to isolated nucleic acid fragments of SEQ ID NO:3 which encode cRNA expressing a biologically active form of tr-CfGluCl, including but not limited to inhibition or promotion of CfGluCl channel activity in the target cell type. Any such polynucleotide includes but is not necessarily limited to nucleotide substitutions, deletions, additions, amino-terminal truncations and carboxy-terminal truncations from the truncated form.

Again, any such truncated nucleic acid molecule (as compared to CfGluCl) may include a deoxyribonucleic acid molecule (DNA), such as genomic DNA and complementary DNA (cDNA), which may be single (coding or non-coding strand) or double stranded, as well as synthetic DNA, such as a synthesized, single stranded polynucleotide. The isolated nucleic acid molecule of the present invention may also include a ribonucleic acid molecule (RNA), including but not limited to messenger RNA (mRNA) or complementary RNA (cRNA) transcribed from a recombinant expression vector comprising a DNA molecule which encodes a truncated version of the full-length C. felis GluCl channel.

The present invention also relates to recombinant vectors and recombinant hosts, both prokaryotic and eukaryotic, which contain the substantially purified nucleic acid molecules disclosed throughout this specification, especially a nucleic acid molecule encoding a truncated version of a C. felis GluCl channel, CfGluCl., such as the cDNA molecule disclosed in FIGS. 3A–B and set forth in SEQ ID NO:3.

The present invention also relates to a substantially purified form of a truncated version of the C. felis GluCl channel, trCfGluCl, and especially the truncated version of the C. felis GluCl channel, which is disclosed in FIG. 4 and as set forth in SEQ ID NO:4, referred to as trCfGluCl-1.

The present invention also relates to biologically active fragments and/or mutants of trCfGluCl-1, including but not necessarily limited to amino acid substitutions, deletions, additions, amino terminal truncations and carboxy-terminal truncations.

Any of a variety of procedures may be used to clone a C. felis GluCl channel. These methods include, but are not limited to, (1) a RACE PCR cloning technique (Frohman, et al., 1988, Proc. Natl. Acad. Sci. USA 85: 8998–9002). 5' and/or 3' RACE may be performed to generate a full-length cDNA sequence. This strategy involves using gene-specific oligonucleotide primers for PCR amplification of C. felis GluCl channel cDNA. These gene-specific primers are designed through identification of an expressed sequence tag (EST) nucleotide sequence which has been identified by searching any number of publicly available nucleic acid and protein databases; (2) direct functional expression of the C. felis GluCl channel cDNA following the construction of a C. felis GluCl channel-containing cDNA library in an appropriate expression vector system; (3) screening a C. felis GluCl channel-containing cDNA library constructed in a bacteriophage or plasmid shuttle vector with a labeled degenerate oligonucleotide probe designed from the amino acid sequence of the C. felis GluCl channel protein; and (4) screening a C. felis GluCl channel-containing cDNA library constructed in a bacteriophage or plasmid shuttle vector with a partial cDNA encoding the C. felis GluCl channel protein. This partial EDNA is obtained by the specific PCR amplification of C. felis GluCl channel DNA fragments through the design of degenerate oligonucleotide primers from the amino acid sequence known for other kinases which are related to the C. felis GluCl channel protein; (5) screening a C. felis GluCl channel-containing cDNA library constructed in a bacteriophage or plasmid shuttle vector with a partial cDNA encoding the C. felis GluCl channel protein. This strategy may also involve using gene-specific oligonucleotide primers for PCR amplification of C. felis GluCl channel cDNA identified as an EST as described above; or (6) designing 5' and 3' gene specific oligonucleotides using SEQ ID NO: 1 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding C. felis GluCl channel.

It is readily apparent to those skilled in the art that suitable cDNA libraries may be prepared from cells or cell lines which have *C. felis* GluCl channel activity. The selection of cells or cell lines for use in preparing a cDNA library to isolate a cDNA encoding *C. felis* GluCl channel may be done by first measuring cell-associated *C. felis* GluCl channel activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding *C. felis* GluCl channel may also be isolated from a suitable genomic DNA library. Construction of genomic DNA libraries can be performed by standard techniques well known in the art. Well known genomic DNA library construction techniques can be found in Sambrook, et al., supra.

In order to clone the *C. felis* GluCl channel gene by one of the preferred methods, the amino acid sequence or DNA sequence of *C. felis* GluCl channel or a homologous protein may be necessary. To accomplish this, the *C. felis* GluCl channel protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial *C. felis* GluCl channel DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the *C. felis* GluCl channel sequence but others in the set will be capable of hybridizing to *C. felis* GluCl channel DNA even in the presence of DNA oligonucleotides with mismatches. The mismatched DNA oligonucleotides may still sufficiently hybridize to the *C. felis* GluCl channel DNA to permit identification and isolation of *C. felis* GluCl channel encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO: 1, either for the purpose of isolating overlapping 5' and 3' RACE products for generation of a full-length sequence coding for *C. felis* GluCl channel, or to isolate a portion of the nucleotide sequence coding for *C. felis* GluCl channel for use as a probe to screen one or more cDNA- or genomic-based libraries to isolate a full-length sequence encoding *C. felis* GluCl channel or *C. felis* GluCl channel-like proteins.

In an exemplified method, a *C. felis* GluCl channel cDNA was generated by screening a *C. felis* cDNA library prepared in the phagemid cloning vector λZAPII (Stratagene, LaJolla, Calif.) This library was screened with a DNA probe corresponding to nucleotides 471 to 1760 of the DrosGluCl cDNA (Cully et al., 1996, *J Biol. Chem.* 271: 20187–20191; accession number U58776) which codes for all but the last four amino acids of the Drosophila glutamate-gated chloride channel. Two positive clones, F5A and F6 were chosen for further analysis. These cDNA clones were shown to encode a truncated polypeptide disclosed in FIG. 4 and SEQ ID NO:4, referred to within this specification as trCfGluCl-1. It is shown in this specification that the truncation at the amino-terminal region of clone F5A produced a frame shift mutation. It is also shown in this specification that this truncation was in fact due to a deletion of 71 nucleotides at the presumptive amino-terminal extracellular domain, resulting in a frame shift mutation that resulted in expression of the truncated protein, trCfGluCl-1. A cDNA fragment containing the missing portion of a putative *C. felis* GluCl channel cDNA was generated by PCR amplification of randomly primed flea cDNA. Primer-1 (5'-CTCAGAGTCAGGATCCGGCTA-3'; SEQ ID NO:5) and Primer-2 (5'-CTGAAAGTTAACTGGACACTG-3'; SEQ ED NO:6) were used in a standard PCR reaction to amplify a 532 bp PCR fragment that was shown by DNA sequence analysis to contain the missing 71 nucleotides and flanking sequences disclosed in the F5A clone. A 517 bp BamHI/HpaI fragment of this PCR product was isolated and inserted into a BamHI/HpaI digested F5A clone to generate the full length cDNA clone designated Flea51, as shown in FIGS. 1A–B. This cDNA molecule contains an open reading frame which encodes a *C. felis* GluCl channel, as shown in FIG. 2, as set forth as SEQ ID NO:2. In addition, the 5' untranslated region the exemplified cDNA which encodes a CfGluCl channel protein was determined and is presented as SEQ ID NO:7.

A variety of mammalian expression vectors may be used to express a recombinant *C. felis* GluCl channel protein in mammalian cells. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

Commercially available mammalian expression vectors which may be suitable for recombinant *C. felis* GluCl channel protein expression, include but are not limited to, pcDNA3.1 (Invitrogen), pLITMUS28, pLITMUS29, pLITMUS38 and pLITMUS39 (New England Bioloabs), pcDNAI, pcDNAIamp (Invitrogen), pcDNA3 (Invitrogen), pMClneo (Stratagene), pXT1 (Stratagene), pSG5 (Stratagene), EBO-pSV2-neo (ATCC 37593) pBPV-1(8–2) (ATCC 37110), pdBPV-MM heo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express a recombinant *C. felis* GluCl channel protein in bacterial cells. Commercially available bacterial expression vectors which may be suitable for recombinant *C. felis* GluCl channel protein expression include, but are not limited to pCR2.1 (Invitrogen), pET11a (Novagen), lambda gt11 (Invitrogen), and pKK223–3 (Pharmacia).

A variety of fungal cell expression vectors may be used to express recombinant *C. felis* GluCl channel protein in fungal cells. Commercially available fungal cell expression vectors which may be suitable for recombinant *C. felis* GluCl channel expression include but are not limited to pYES2 (Invitrogen) and Pichia expression vector (Invitrogen).

A variety of insect cell expression vectors may be used to express recombinant receptor in insect cells. Commercially available insect cell expression vectors which may be suitable for recombinant expression of a *C. felis* GluCl channel protein include but are not limited to pBlueBacIII and pBlueBacHis2 (Invitrogen), and pAcG2T (Pharmingen).

An expression vector containing DNA encoding a *C. felis* GluCl channel protein and/or *C. felis* GluCl channel-like protein may be used for expression of *C. felis* GluCl channel protein in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to Drosophila- and silkworm-derived cell lines. Cell lines derived from mammalian species which may be suitable and which are commercially available, include but are not limited to, L cells L-M(TK—) (ATCC CCL 1.3), L cells LM (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-KI (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209).

The cloned human *C. felis* GluCl channel cDNA obtained through the methods described above may be recombinantly expressed by molecular cloning into an expression vector (such as pcDNA3.1, pCR2.1, pBlueBacHis2 and pLITMUS28) containing a suitable promoter and other appropriate transcription regulatory elements, and transferred into prokaryotic or eukaryotic host cells to produce recombinant *C. felis* GluCl channel protein. Techniques for such manipulations can be found described in Sambrook, et al., supra, are discussed at length in the Example section and are well known and easily available to the artisan of ordinary skill in the art.

The expression vector may be introduced into host cells via any one of a number of techniques including but not limited to direct injection, transformation, transfection, protoplast fusion, lipofection, and electroporation. The expression vector-containing cells are clonally propagated and individually analyzed to determine whether they produce *C. felis* GluCl protein. Identification of *C. felis* GluCl expressing host cell clones may be done by several means, including but not limited to immunological reactivity with anti-*C. felis* GluCl antibodies, and the presence of host cell-associated GluCl activity.

Expression of *C. felis* GluCl DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the *C. felis* GluCl channel cDNA sequence (s) that yields optimal levels of *C. felis* GluCl channel protein, cDNA molecules including but not limited to the following can be constructed: a cDNA fragment containing the full-length open reading frame for *C. felis* GluCl channel protein as well as various constructs containing portions of the cDNA encoding only specific domains of the protein or rearranged domains of the protein. All constructs can be designed to contain none, all or portions of the 5' and/or 3' untranslated region of a *C. felis* GluCl channel cDNA. The expression levels and activity of *C. felis* GluCl channel protein can be determined following the introduction, both singly and in combination, of these constructs into appropriate host cells. Following determination of the *C. felis* GluCl channel cDNA cassette yielding optimal expression in transient assays, this *C. felis* GluCl channel cDNA construct is transferred to a variety of expression vectors (including recombinant viruses), including but not limited to those for expression in host cells including, but not limited to, mammalian cells, insect cells such as baculovirus-infected insect cells, oocytes such as Xenopus oocytes, bacterial such as*E. coli*, and the yeast *S. cerevisiae*.

The present invention also relates to methods of expressing an active *C. felis* GluCl channel protein and biological equivalents disclosed herein, assays employing these recombinantly expressed gene products, cells expressing these gene products, and agonistic and/or antagonistic compounds identified through the use of assays utilizing these recombinant forms, including, but not limited to, one or more modulators of a *C. felis* GluCl channel.

A preferred expression system for the electrophysiological-based assays and related improved methods of measuring glutamate-gated chloride channel activity and modulation comprise injecting nucleic acid molecules into *Xenopus laevis oocytes*. The general use of *Xenopus oocytes* in the study of ion channel activity is known in the art (Dascal, 1987, *Crit. Rev. Biochem.* 22: 317–317; Lester, 1988, *Science* 241: 1057–1063; see also *Methods of Enzymology*, Vol. 207, 1992, Ch. 14–25, Rudy and Iverson, ed., Academic Press, Inc., New York). A portion of the present invention discloses an improved method of measuring channel activity and modulation by agonists and/or antagonists which is several-fold more sensitive than previously disclosed. The Xenopus oocytes are injected with nucleic acid material, including but not limited to DNA, mRNA or cRNA which encode a gated-channel, wherein channel activity may be measured as well as response of the channel to various modulators. To this end, the present invention relates to an improved in vitro method of measuring ion channel activity in eukaryotic cells, especially Xenopus oocytes, which comprises utilizing a holding potential more positive than the reversal potential for chloride (i.e, greater than −30 mV), preferably about 0 mV. This alteration in assay measurement conditions has resulting in a 10-fold increase in sensitivity of the assay to modulation by ivermectin phosphate. Therefore, this improved assay will allow screening and selecting for compounds which modulate GluCl activity at levels which were previously thought to be undetectable. Data is presented in Example Section 2 which exemplifies the use of this improved assay for detecting expressed ion channel activity in Xenopus oocytes. It will be evident to the skilled artisan that this improved method may be utilized in various ion channel measurement assays, and especially assays which measure glutamate-gated activity in a eukaryotic cell, such as a *Xenopus oocyte.* It is especially preferred that invertebrate glutamate-gated chloride channels, including but in not way limited to *Caenorhabditis elegans, Drosophila melonogaster* and *Ctenocephalides felis* glutamate-gated channel proteins, be utilized in an assay to screen and select for compounds which modulate the activity of these channels.

Levels of C. felis GluCl protein in host cells are quantitated by immunoaffinity and/or ligand affinity techniques. Cells expressing GluCl can be assayed for the number of GluCl molecules expressed by measuring the amount of radioactive glutamate or ivermectin binding to cell membranes. GluCl-specific affinity beads or GluCl-specific antibodies are used to isolate for example $^{35}$S-methionine labelled or unlabelled GluCl protein. Labelled GluCl protein is analyzed by SDS PAGE. Unlabelled GluCl protein is detected by Western blotting, ELISA or RIA assays employing GluCl specific antibodies.

Recombinant C. felis GluCl channel protein can be separated from other cellular proteins by use of an immunoaffinity column made with monoclonal or polyclonal antibodies specific for full-length C. felis GluCl channel protein, or polypeptide fragments of C. felis GluCl channel protein. Additionally, polyclonal or monoclonal antibodies may be raised against a synthetic peptide (usually from about 9 to about 25 amino acids in length) from a portion of the protein as disclosed in SEQ ID NO:2. Monospecific antibodies to C. felis GluCl channel are purified from mammalian antisera containing antibodies reactive against a C. felis GluCl channel or are prepared as monoclonal antibodies reactive with aC. fetis GluCl channel using the technique of Kohler and Milstein (1975, Nature 256: 495–497). Monospecific antibody as used herein is defined as a single antibody species or multiple antibody species with homogenous binding characteristics for aC. felis GluCl channel. Homogenous binding as used herein refers to the ability of the antibody species to bind to a specific antigen or epitope, such as those associated with a C. felis GluCl channel, as described above. C. felis GluCl channel protein-specific antibodies are raised by immunizing animals such as mice, rats, guinea pigs, rabbits, goats, horses and the like, with an appropriate concentration of C. felis GluCl channel protein or a synthetic peptide generated from a portion of C. felis GluCl channel with or without an immune adjuvant. Therefore, the present invention also relates to polyclonal and monoclonal antibodies raised in response to the C. felis GluCl channel protein disclosed herein, or a biologically active fragment thereof.

Preimmune serum is collected prior to the first immunization. Each animal receives between about 0.1 μg and about 1000 μg of C. felis GluCl channel protein associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consists of C. felis GluCl channel protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of C. felis GluCl channel in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with C. felis GluCl channel are prepared by immunzing inbred mice, preferably Balb/c, with C. felis GluCl channel protein. The mice are immunized by the IP or SC route with about 1 μg to about 100's, preferably about 10's, of C. felis GluCl channel protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100's of C. felis GluCl channel protein in a buffer solution such as phosphate buffered saline by the intravenous (I) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4–1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using C. felis GluCl channel protein as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about 2×10$^6$ to about 6×10$^6$ hybridoma cells about 4 days after priming. Ascites fluid is collected at approximately 8–12 days after cell transfer and the monoclonal antibodies are purified by techniques known in the art.

In vitro production of anti-C. felis GluCl channel protien mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of *C. felis* GluCl channel protein in body fluids or tissue and cell extracts.

It is readily apparent to those skilled in the art that the above described methods for producing monospecific antibodies may be utilized to produce antibodies specific for *C. felis* GluCl channel peptide fragments, or full-length *C. felis* GluCl channel protein.

*C. felis* GluCl channel antibody affinity colulmns are made, for example, by adding the antibodies to Affigel-10 (Biorad), a gel support which is pre-activated with N-hydroxysucciiimde esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing full-length C. felis GluCl channel protein or C. felis GluCl channel protein fragments are slowly passed through the column. The column is then washed with phosphate buffered saline until the optical density (A280) falls to background, then the protein is eluted with 0.23M glycine-HCl (pH 2.6). The purified C. felis GluCl channel protein is then dialyzed against phosphate buffered saline.

Levels of C. felis GluCl channel protein in host cells is quantified by a variety of techniques including, but not limited to, immunoaffinity and/or ligand affinity techniques. *C. felis* GluCl channel protein-specific affinity beads or *C. felis* GluCl channel protein-specific antibodies are used to isolate $^{35}S$-methionine labeled or unlabelled *C. felis* GluCl channel protein. Labeled *C. felis* GluCl channel protein is analyzed by SDS-PAGE. Unlabelled *C. felis* GluCl channel protein is detected by Western blotting, ELISA or RIA assays employing *C. felis* GluCl channel protein specific antibodies.

Following expression of *C. felis* GluCl channel protein in a host cell, *C. felis* GluCl channel protein may be recovered to provide C. felis GluCl channel protein in active form. Several *C. felis* GluCl channel protein purification procedures are available and suitable for use. Recombinant *C. felis* GluCl channel protein may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography. It is also possible to prepare membrane preparations from a recombinant host cell which contains a recombinant vector which expresses an active *C. felis* GluCl channel. Such membrane preparations from recombinant cells will be useful for in vitro-based screening assays for compounds which modulate *C. felis* GluCl channel activity.

Compounds identified according to the methods disclosed herein may be used alone at appropriate dosages defined by routine testing in order to obtain optimal inhibition of the GluCl receptor or its activity while minimizing any potential toxicity. In addition, co-administration or sequential administration of other agents may be desirable.

The method of the present invention also has the objective of providing suitable topical, oral, systemic and parenteral pharmaceutical formulations for use in the novel methods of treatment of the present invention. The compositions containing compounds identified according to this invention as the active ingredient for use in the modulation of GluCl receptors can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a GluCl modulating agent.

The daily dosage of the products may be varied over a wide range from 0.001 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The dosages of the GluCl receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds active in the method of the present invention may be administered in a single daily dose, or the total daily dosage may be administered in divided doses of two, three or four times daily. Furthermore, compounds active in the method of the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds active in the method of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds active therein can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds active in the method of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds active in the method of the present invention may also be delivered by the use of monoclonal antibodies as individual carriers to which the compound molecules are coupled. The compounds active in the method of the present invention may also be coupled with soluble polymers as targetable drug carriers. Such polymers can include polyvinyl-pyrrolidone, pyran copolymer, polyhydroxy-propylmethacryl-amidephenol, polyhydroxy-ethylaspartamidephenol, or polyethyl-eneoxidepolylysine substituted with palmitoyl residues. Furthermore, the compounds active in the method of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds that are active in the methods of the present invention are useful as antiparastic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animas referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Diseases caused by ectoparasitic arthropods such as ticks, mites, lice, stable flies, hornflies, blowflies, fleas, and other biting insects such as Tenophalides, Ixodes, Psoroptes, Lucilia, and Hemotobia, are also a serious problem. hafection and infestation by these parasites results in loss of blood, skin lesions, and can interfere with normal eating habits thus causing weight loss. These infections can also result in transmission of serious diseases such as encephalitis, anaplasmosis, swine pox, and the like which can be fatal. The compounds that are active in the method disclosed herein are useful for the prevention and treatment of these infections and infestations.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have activity against these parasites, and in addition are also active against Dirofilaria in dogs, Nematospiroides and Syphacia in rodents, biting insects, and migrating diperous larvae such as Hypoderma sp. in cattle, and Gastrophilus in horses.

The compounds active in the method disclosed herein are also useful against endo and ecto parasites which cause parasitic diseases in humans. Examples of such endoparasites which infect man include gastrointestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The active compounds are active against these endo and ecto parasites and in addition are also active against biting insects and other dipterous pests which annoy humans.

The compounds active in the method disclosed herein are also useful against common household pests such as Blatella sp. (cockroach), Tineola sp. (clothes moth), Attagenus sp. (carpet beetle), Musca domestica (housefly) and against Solenopsis Invicta (imported fire ant).

The compounds active in the method disclosed herein are furthermore useful against agricultural pests such as aphids (Acyrthiosiphon sp.), locusts, spider mites, and boll weevils as well as against insect pests which attack stored grains such as Tribolium sp. and Tenebrio sp., and against immature stages of insects living on plant tissue. The compounds are also useful as a nematodicide for the control of soil nematodes and plant parasites such as Meloidogyne sp., which may be agriculturally important.

For use as an antiparasitic agent in animals the compounds may be administered internally either orally, or by injection, or topically as a liquid drench or as a shampoo.

For oral administration, the compounds active in the method disclosed herein may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds active in the method disclosed herein may alternatively be administered parenterally via injection of a formulation consisting of the active ingredient dissolved in an inert liquid carrier. Injection may be either intramuscular, intramural, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds active in the method disclosed herein is possible through the use of a liquid drench or a shampoo containing the instant compounds as an aqueous solution, dispersion or suspension. These formulations generally contain a suspending agent such as bentonite, a wetting agent or the like excipient, and normally will also contain an antifoaming agent. Formulations containing from 0.001 to 1% by weight of the active ingredient are acceptable. Preferred formulations are those containing from 0.01 to 1% by weight of the active compounds.

The compounds active in the method disclosed herein are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds may be used individually or in combination with each other or with other unrelated antiparasitic agents. The dosage of the compounds required for best results depends on several factors such as the species and size of the animal, the type and severity of the infection, the method of administration and the compound used. Oral administration of the compounds at a dose level of from 0.0005 to 10 mg per kg of animal body weight, either in a single dose or in several doses spaced a few days apart, generally gives good results. A single dose of one of the compounds normally gives excellent control however repeat doses may be given to combat re-infection or for parasite species which are unusually persistent. The techniques for administering these compounds to animals are known to those skilled in the veterinary field.

The compounds active in the method disclosed herein may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

Pharmaceutically useful compositions comprising modulators of the *C. felis* GluCl channel may be formulated according to known methods such as by the admixture of a pharmaceutically acceptable carrier. Examples of such carriers and methods of formulation may be found in Remington's Pharmaceutical Sciences.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

The present invention is also directed to methods for screening for compounds which modulate the expression of DNA or RNA encoding *C. felis* GluCl as well as the function of the *C. felis* GluCl protein in vivo. Compounds which modulate these activities may be DNA, RNA, peptides, proteins, or non-proteinaceous organic molecules. Compounds may modulate by increasing or attenuating the expression of DNA or RNA encoding *C. felis* GluCl, or the function of the *C. felis* GluCl protein. Compounds that modulate the expression of DNA or RNA encoding *C. felis* GluCl or the function of *C. felis* GluCl protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, insecticides and anthelminthics.

Kits containing *C. felis* GluCl DNA, antibodies to *C. felis* GluCl, or *C. felis* GluCl protein may be prepared. Such kits are used to detect DNA which hybridizes to *C. felis* GluCl DNA or to detect the presence of *C. felis* GluCl protein or peptide fragments in a sample. Such characterization is useful for a variety of purposes including but not limited to forensic analyses and epidemiological studies.

The DNA molecules, RNA molecules, recombinant protein and antibodies of the present invention may be used to screen and measure levels of *C. felis* GluCl DNA, RNA or protein. The recombinant proteins, DNA molecules, RNA molecules and antibodies lend themselves to the formulation of kits suitable for the detection and typing of *C. felis* GluCl. Such a kit would comprise a compartmentalized carrier suitable to hold in close confinement at least one container. The carrier would further comprise reagents such as recombinant C. felis GluCl protein or anti-GluCl antibodies suitable for detecting GluCl. The carrier may also contain a means for detection such as labeled antigen or enzyme substrates or the like.

Nucleotide sequences that are complementary to the C. felis GluCl encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other GluCl antisense oligonucleotide mimetics. *C. felis* GluCl antisense molecules may be introduced into cells by microinjection, liposome encapsulation or by expression from vectors harboring the antisense sequence. *C. felis* GluCl antisense therapy may be particularly useful for the treatment of diseases where it is beneficial to reduce GluCl activity.

*C. felis* GluCl DNA may be used to introduce GluCl into the cells of target organisms. The GluCl gene can be ligated into viral vectors which mediate transfer of the GluCl DNA by infection of recipient host cells. Suitable viral vectors include retrovirus, adenovirus, adeno-associated virus, herpes virus, vaccinia virus, polio virus and the like. Alternatively, GluCl DNA can be transferred into cells by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo GluCl gene therapy. GluCl gene therapy may be particularly useful where it is beneficial to elevate GluCl activity.

The present invention also provides for improved methods of screening for modulators of a GluCl channel in general and modulators of the *C. felis* GluCl channel in particular. It is shown in Example Section 2 that improved assay conditions result in a 10-fold increase in channel modulator sensitivity when compared to previous known assay conditions. In a preferred aspect of measuring GluCl channel activity, oocytes are injected with synthetic RNAs or DNAs for one or more *C. felis* GluCl proteins. Following an appropriate period of time to allow for expression, GluCl activity is measured by specific ligand binding and electrophysiological characteristics of the host cells expressing GluCl DNA. Voltage-clamp studies were conducted as described in Example Section 2, preferably utilizing a holding potential of 0 mV during measurements of modulation by ivermectin phosphate. Exemplification of this improved method of a cell-based assay of GluCl channel activity is shown in Example Section 2 and is further detailed in FIGS. 5A and 5B (showing activation of CfGluCl-1 by glutamate), FIG. 6 (showing that the CfGluCl-1 channel is selective for chloride), and FIGS. 7A and 7B (showing that IVM-$PO_4$ is an agonist of a GluCl channel).

The following examples are provided to illustrate the present invention without, however, limiting the same hereto.

EXAMPLE 1

Isolation and Characterization of a Full Length cDNA Encoding a *Ctenocephalides felis* GluCl Channel

*Ctenocephalides felis* Poly $A^+$ RNA isolation—Poly$(A)^+$ RNA was prepared from whole fleas. The fleas were rapidly frozen in liquid $N_2$ and ground with a mortar and pestle while submerged in liquid $N_2$. The frozen, powdered *C. felis* tissue was added to a solution containing 4M guanidinium thiocyanate, 5 mM sodium citrate pH 7.0, and 0.1M β-mercaptoethanol (1 gm tissue/10 ml solution), and was mixed with a polytron homogenizer. After 1 minute of homogenization, 0.5% sodium sarkosyl was added and mixed well and the solution was centrifuged at 10,000 rpm for 10 minutes. The supernatant was layered over a 5.7M CsCl cushion and centrifuged for 18 hours at 33,000 rpm. The RNA pellet was washed with 70% ethanol, resuspended in $H_2O$ and extracted with chloroform:isobutanol, 4:1 and precipitated with ethanol. Poly $(A)^+$ RNA was isolated by two rounds of purification on oligo (dT)-cellulose columns.

Isolation of a cDNA Partially Encoding a *C.felis* GluCl Channel—An oligo-dT primed *C. felis* cDNA library was prepared in the phagemid cloning vector λZAPII (Stratagene, LaJolla, Calif.) This library was transfected into *E. coli* PLK-F' cells, plated on NZY medium (Sambrook, et al, 1989, *Molecular Cloning: A Laboratory Manual,* Second Edition, Cold Spring Harbor Laboratory Press, Cold Spring Harbor, N.Y.), and incubated 18 hrs. at 37° C. The resultant plaques were transferred to Durulose membranes (Stratagene). The membranes were prehybridized in 50% formamide; 2× Denhardts solution; 5× SSPE; 0.1%SDS; 100 μg/ml solmon sperm DNA for 16 hours and hybridized in the above prehybridization solution containing 10% dextran sulfate for 24 hours with $2\times10^7$ cpm a hybridization probe was a PCR-generated fragment of the DrosGluCl cDNA corresponding to nucleotides 471–1760 of the cDNA as listed in GenBank (Cully, et al., 1996, *J. Biol. Chem.* 271(33): 20187–20191; accession number U58776). This DNA codes for all but the last four amino acids of the mature Drosophila glutamate-gated chloride channel. The filters were washed at 52° C. in 6×SSC, 0.1% SDS. The washed filters were exposed to X-ray film. Two positive clones, F5A and F6 were chosen for further analysis. These clones were converted into plasmids by in vivo excision as per the Stratagene protocol. Clone F5A was subjected to DNA sequence analysis and is disclosed in FIG. 3 and SEQ ID NO:3, and as follows:

```
ATGGACAGCA TTAGTTTGCT CCTACTTTTG ATAACATGTC TAAGTCTACA

CACATGCTTA TCTGCAAATG CAAAACCTCG TCTAGGAGGC GGCAAAGAAA

ATTTCAGGGC CAAAGAAAAG CAAGTTCTGG ACCAAATTTT AGGCCCAGGC

CATTACGATG CCAGAATAAG GCCTTCTGGA GTCAATGGAA CTGGAATACA

GTGTCCAGTT AACTTTCAGG GAACAATGGC AGGATGAGAG GTTGAAATTT
```

-continued

```
AACGACTTTG GAGGTCGTTT AAAATACTTA ACACTAACCG AAGCAAGTCG

TGTATGGATG CCCGATTTGT TCTTTGCGAA TGAAAAGGAG GGCCACTTTC

ACAACATCAT CATGCCGAAC GTCTACATTC GTATTTTTCC TTACGGTTCC

GTACTATACA GCATCAGGAT ATCGCTTACT TTGGCGTGTC CTATGAATCT

GAAACTGTAT CCGCTCGATA GGCAGGTGTG CTCTCTCCGG ATGGCCAGTT

ATGGTTGGAC CACAAACGAT CTGGTGTTTT TGTGGAAGGA AGGTGACCCG

GTGCAGGTTG TCAAGAATCT ACATCTGCCC AGGTTTACGT TGGAGAAGTT

CTTGACGGAT TATTGTAACA GCAAAACCAA TACCGGTGAA TACAGTTGCC

TGAAGGTCGA CCTGCTCTTT AAACGAGAGT TCTCGTACTA CCTGATCCAG

ATCTACATTC CTTGTTGCAT GTTGGTGATC GTTTCCTGGG TGTCGTTCTG

GTTGGACCAG GGAGCGGTTC CGGCCAGAGT ATCACTGGGT GTGACCACTC

TCCTCACCAT GGCCACCCAG ACGTCGGGCA TAAACGCCTC CCTGCCGCCA

GTGTCCTACA CAAAAGCCAT CGACGTCTGG ACCGGAGTCT GCCTCACGTT

CGTCTTCGGG GCTTTGCTCG AATTCGCCCT CGTCAACTAC GCCTCCAGAT

CCGATATGCA CAGGGAAAAC ATGAAGAAAA AGCGCAGGGA ACTTGAACAA

GCAGCCAGCC TGGACGCCGC CTCCGACCTG ATGGACGGCA CTGATGGCAC

TTTTGCTATG AAGCCTCTGG TACGCCACTC CGTCGACGCC GTCGGTCTCG

ATAAGGTTCG TCAGTGCGAG ATACACATGC AGCCGGCGTC CAGGCAGAAC

TGCTGCAGGA GCTGGATAAG CAAATTCCCG ACGAGGTCGA AACGCATCGA

CGTCATATCA AGAATCACTT TCCCGCTGGT GTTTGCTTTG TTCAATCTGG

TGTACTGGTC GACCTATTTG TTCAGGGACG AGGCGGAGGA GAATTAG (SEQ ID NO:3).
```

Clone F5A was shown to encode a truncated polypeptide disclosed in FIG. 4 and SEQ ID NO:4, referred to within this specification as trCfGluCl-1, and disclosed as follows:

```
1  MDSISLLLLL ITCLSLHTCL SANAKPRLGG GKENFRAKEK QVLDQILGPG

51 HYDARIRPSG VNGTGIQCPV NFQGTMAG (SEQ ID NO:4).
```

Isolation of a cDNA Encoding a *C. felis* GluCl Channel—It was determined that clone F5A lacked an internal portion a possible *C. felis* GluCl channel cDNA at the presumptive amino-terminal extracellular domain, resulting in a frame shift mutation and the concomitant truncated protein, trCfGluCl-1. A cDNA fragment containing the missing portion of a putative *C. felis* GluCl channel cDNA was generated by PCR amplification of randomly primed flea cDNA. Primer-1 (CTCAGAGTCAGGATCCGGCTA; SEQ ID NO:5) and Primer-2 (CTGAAAGTTAACTGGACACTG; SEQ ID NO:6) were used in a standard PCR reaction to amplify a 532 bp PCR fragment that was shown by DNA sequence analysis to contain the missing 71 nucleotides and flanking sequences disclosed in the F5A clone. This PCR fragment is as follows:

```
TCAGAGTCA GGATCC GGCTA TATTGGACGA TATGCTGCAT GGTCCCTGTC

ATACAAATAC TCCTTCGCCT TCACTGGAAC CAACCAAGAC TGTCCCCACG

TGTCCGACAT CAGTTGAAGG AAATTCTGTG ACGACATGGC AACACTTTTG
```

-continued

```
TTCAGGAACA ACAATAACAT CATCGACACA GAATATCGGC GAAGCCTATT

CTTCGATTCA AGAAGAAGAA TTTCTTCACT TTATCTTCAG GGATGGACAG

CATTAGTTTG CTCCTACTTT TGATAACATG TCTAAGTCTA CACACATGCT

TATCTGCAAA TGCAAAACCT CGTCTAGGAG GCGGCAAAGA AAATTTCAGG

GCCAAAGAAA AGCAAGTTCT GGACCAAATT TTAGGCCCAG GCCATTACGA

TGCCAGAATA AGGCCTTCTG GAGTCAATGG AACTGGAGAC GGTCCGACCG

TGGTAGCAGT CAACATCTAT CTGAGATCAA TCAGCGAAAT AGATGACTAC

AAAATGGAAT ACAGTGTCCA GTTAAC TTTC AG (SEQ ID NO:8)
```

This PCR fragment was cloned using the TA cloning vector kit (Invitrogen) and individual clones were sequenced to identify those lacking PCR artifacts and containing the missing 71 bp fragment. A 517 bp BamHI/HpaI fragment (Bam HI-GGATCC; HpaI GTTAAC, as underlined above) of this PCR product was isolated and inserted into a BamHI/HpaI digested F5A clone (FIG. 3; SEQ ID NO:3) to generate the full length cDNA clone in the F5A pBS vector, designated Flea51, shown in FIG. 1, and set forth as SEQ ID NO:1 as follows:

```
ATGGACAGCA TTAGTTTGCT CCTACTTTTG ATAACATGTC TAAGTCTACA

CACATGCTTA TCTGCAAATG CAAAACCTCG TCTAGGAGGC GGCAAAGAAA

ATTTCAGGGC CAAAGAAAAG CAAGTTCTGG ACCAAATTTT AGGCCCAGGC

CATTACGATG CCAGAATAAG GCCTTCTGGA GTCAATGGAA CTGGAGACGG

TCCGACCGTG GTAGCAGTCA ACATCTATCT GAGATCAATC AGCGAAATAG

ATGACTACAA AATGGAATAC AGTGTCCAGT TAACTTTCAG GGAACAATGG

CAGGATGAGA GGTTGAAATT TAACGACTTT GGAGGTCGTT TAAAATACTT

AACACTAACC GAAGCAAGTC GTGTATGGAT GCCCGATTTG TTCTTTGCGA

ATGAAAAGGA GGGCCACTTT CACAACATCA TCATGCCGAA CGTCTACATT

CGTATTTTTC CTTACGGTTC CGTACTATAC AGCATCAGGA TATCGCTTAC

TTTGGCGTGT CCTATGAATC TGAAACTGTA TCCGCTCGAT AGGCAGGTGT

GCTCTCTCCG GATGGCCAGT TATGGTTGGA CCACAAACGA TCTGGTGTTT

TTGTGGAAGG AAGGTGACCC GGTGCAGGTT GTCAAGAATC TACATCTGCC

CAGGTTTACG TTGGAGAAGT TCTTGACGGA TTATTGTAAC AGCAAAACCA

ATACCGGTGA ATACAGTTGC CTGAAGGTCG ACCTGCTCTT TAAACGAGAG

TTCTCGTACT ACCTGATCCA GATCTACATT CCTTGTTGCA TGTTGGTGAT

CGTTTCCTGG GTGTCGTTCT GGTTGGACCA GGGAGCGGTT CCGGCCAGAG

TATCACTGGG TGTGACCACT CTCCTCACCA TGGCCACCCA GACGTCGGGC

ATAAACGCCT CCCTGCCGCC AGTGTCCTAC ACAAAAGCCA TCGACGTCTG

GACCGGAGTC TGCCTCACGT TCGTCTTCGG GGCTTTGCTC GAATTCGCCC

TCGTCAACTA CGCCTCCAGA TCCGATATGC ACAGGGAAAA CATGAAGAAA

AAGCGCAGGG AACTTGAACA AGCAGCCAGC CTGGACGCCG CCTCCGACCT

GATGGACGGC ACTGATGGCA CTTTTGCTAT GAAGCCTCTG GTACGCCACT

CCGTCGACGC CGTCGGTCTC GATAAGGTTC GTCAGTGCGA GATACACATG

CAGCCGGCGT CCAGGCAGAA CTGCTGCAGG AGCTGGATAA GCAAATTCCC
```

-continued

```
GACGAGGTCG AAACGCATCG ACGTCATATC AAGAATCACT TTCCCGCTGG

TGTTTGCTTT GTTCAATCTG GTGTACTGGT CGACCTATTT GTTCAGGGAC

GAGGCGGAGG AGAATTAG (SEQ ID NO:1).
```

This cDNA molecule contains an open reading frame which encodes a *C. felis* GluCl channel, as shown in FIG. 2, as set forth as SEQ ID NO:2, and as follows:

```
MDSISLLLLL ITCLSLHTCL SANAKPRLGG GKENFRAKEK QVLDQILGPG

HYDARIRPSG VNGTGDGPTV VAVNIYLRSI SEIDDYKMEY SVQLTFREQW

QDERLKFNDF GGRLKYLTLT EASRVWMPDL FFANEKEGHF HNIIMPNVYI

RIFPYGSVLY SIRISLTLAC PMNLKLYPLD RQVCSLRMAS YGWTTNDLVF

LWKEGDPVQV VKNLHLPRFT LEKFLTDYCN SKTNTGEYSC LKVDLLFKRE

FSYYLIQIYI PCCMLVIVSW VSFWLDQGAV PARVSLGVTT LLTMATQTSG

INASLPPVSY TKAIDVWTGV CLTFVFGALL EFALVNYASR SDMHRENMKK

KRRELEQAAS LDAASDLMDG TDGTFAMKPL VRHSVDAVGL DKVRQCEIHM

QPASRQNCCR SWISKFPTRS KRIDVISRIT FPLVFALFNL VYWSTYLFRD

EAEEN (SEQ ID NO:2).
```

In addition, the 5' untranslated region the exemplified cDNA which encodes a CfGluCl channel protein was determined and is presented as SEQ ID NO:7, and as follows:

```
AACTAGTGGA TCCCCCGGGC TGCAGGATTC GGCACGAGAA TTTTTTAAAA

TAATCCTCAA CAGCATGATA CAAGAGGATG ATTTTATGAT CCCTGTAAAC

ACTTGCTTGA ATTTTAGATT GCAACTGGAG GCTCCGCTGA CACTCTCTCT

TGTTCGAGCA CAGGAATTGC TCGACATCTG GTCAAACGCG GGCTACTTCA

TAATATCCGA CGATGACAAT TTAATGTTCG GAGCAAGAAC AATTGCAGAA

TTTGAAGTGT ACTTTAACGA TACATTCGAA GGACGCATGA AAATGTGCAC

GATGTGCATG TTGCCCACCT TCTATTGACC AGCAAGCACC CCTTCGCCGG

TGAGCATGTC ACCCACCGAC AGGCGCCTTC TGTGCGCCCT CGACGACCTG

CACTTAGCGG TTGCTAAGAA GCCCTAAGAA GCCGAGACGG TTCGCTTCGC

CCGGGGGCGA TTCCTCACGA TGCACAAGCG GAGGCGCAAG AGGCTGACGA

CGAGGAGCCT CAGAGTCAGG ATCCGGCTAT ATTGGACGAT ATGCTGCATG

GTCCCTGTCA TACAAATACT CCTTCGCCTT CACTGGAACC AACCAAGACT

GTCCCCACGT GTCCGACATC AGTTGAAGGA AATTCTGTGA CGACATGGCA

ACACTTTTGT TCAGGAACAA CAATAACATC ATCGACACAG AATATCGGCG

AAGCCTATTC TTCGATTCAA GAAGAAGAAT TTCTTCACTT TATCTTCAGG

G (SEQ ID NO:7)
```

EXAMPLE 2

Expression of the CfGluCl-1 protein in *Xenopus* oocytes

The full-length cDNA encoding CfGluCl-1 in plasmid vector pBluescript (Stratagene, LaJolla, Calif.) is linearized and capped cRNA transcripts are synthesized using appropriate oligonucleotide primers and the mMESSAGE mMACHINE in vitro RNA transcription kit (Ambion). *Xenopus laevis* oocytes were prepared and injected using standard methods as described (Arena et al., 1991, *Mol. Pharmacol.* 40: 368–374; Arena et al, 1992, *Mol. Brain Res.* 15: 339–348). Adult female *Xenopus laevis* were anesthetized with 0.17% tricaine methanesulfonate and the ovaries were surgically removed and placed in a dish consisting of (mM): NaCl 82.5, KCl 2, MgCl2 1, CaCl$_2$ 1.8, HEPES 5 adjusted to pH 7.5 with NaOH (OR-2). Ovarian lobes were broken open, rinsed several times, and gently shaken in OR-2 containing 0.2% collagenase (Sigma, Type IA) for 2–5 hours. When approximately 50% of the follicular layers were removed, Stage V and VI oocytes were selected and placed in media consisting of (mM): NaCl 86, KCl 2, MgCl2 1, CaCl2 1.8, HEPES 5, Na pyruvate 2.5, theophylline 0.5, gentamicin 0.1 adjusted to pH 7.5 with NaOH (ND-96) for 2448 hours before injection. For most experiments, oocytes were injected with 10 ng of cRNA in 50 nl of RNase free water. Control oocytes were injected with 50 nl of water. Oocytes were incubated for 1–5 days in ND-96 supplemented with 50 mg/ml gentamycin, 2.5 mM Na pyruvate and 0.5 mM theophylline before recording. Incubations and collagenase digestion were carried out at 180° C.

Voltage-clamp studies were conducted with the two microelectrode voltage clamp technique using a Dagan CA1 amplifier (Dagan Instruments, Minneapolis, Minn.). The current passing microelectrodes were filled with 0.7M KCl plus 1.7M K$_3$-citrate and the voltage recording microelectrodes were filled with 1.0M KCl. The extracellular solution for most experiments was saline consisting of (mM): NaCl 96, BaCl$_2$ 3.5, MgCl$_2$ 0.5, CaCl$_2$ 0.1, HEPES 5, adjusted to pH 7.5 with NaOH. The extracellular chloride concentration was reduced in some experiments by equimolar replacement of NaCl with the sodium salt of the indicated anion. Experiments were conducted at 21–24° C. Data were acquired using the program Pulse and most analysis was performed with the companion program Pulsefit (Instrutech Instruments, Great Neck, N.Y.) or with Igor Pro (Wavemetrics, Lake Oswego, Oreg.). Data were filtered (fc, –3db) at 1 kHz, unless otherwise indicated.

Figure 5B:
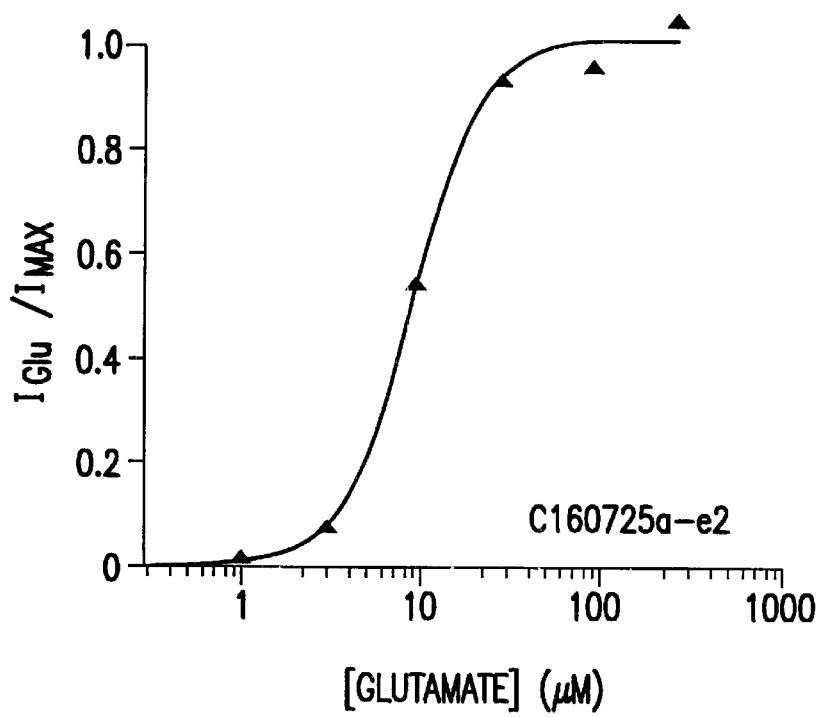

FIG. 5A and FIG. 5B show the activation of CfGluCl-1 by glutamate. FIG. 5A shows superimposed current recordings in response to 10, 30, 100 and 300 μM glutamate. The duration of exposure to glutamate is indicated by the solid bar at top. FIG. 5B shoes the concentration-response curve for glutamate. Peak outward current is plotted vs. glutamate concentration. The solid curve is the best fit to the equation $I/I_{max} = \{1 + (EC_{50}/[\text{glutamate}])^n\}^{-1}$. For the experiment shown in FIG. 5B, $EC_{50}=9.3$ μM, n=2.13. Agonists for other types of ligand-gated chloride channels were also tested for the ability to activate CfGluCl-1. GABA, glycine, histamine, acetylcholine and muscimol were all inactive.

Figure 6:
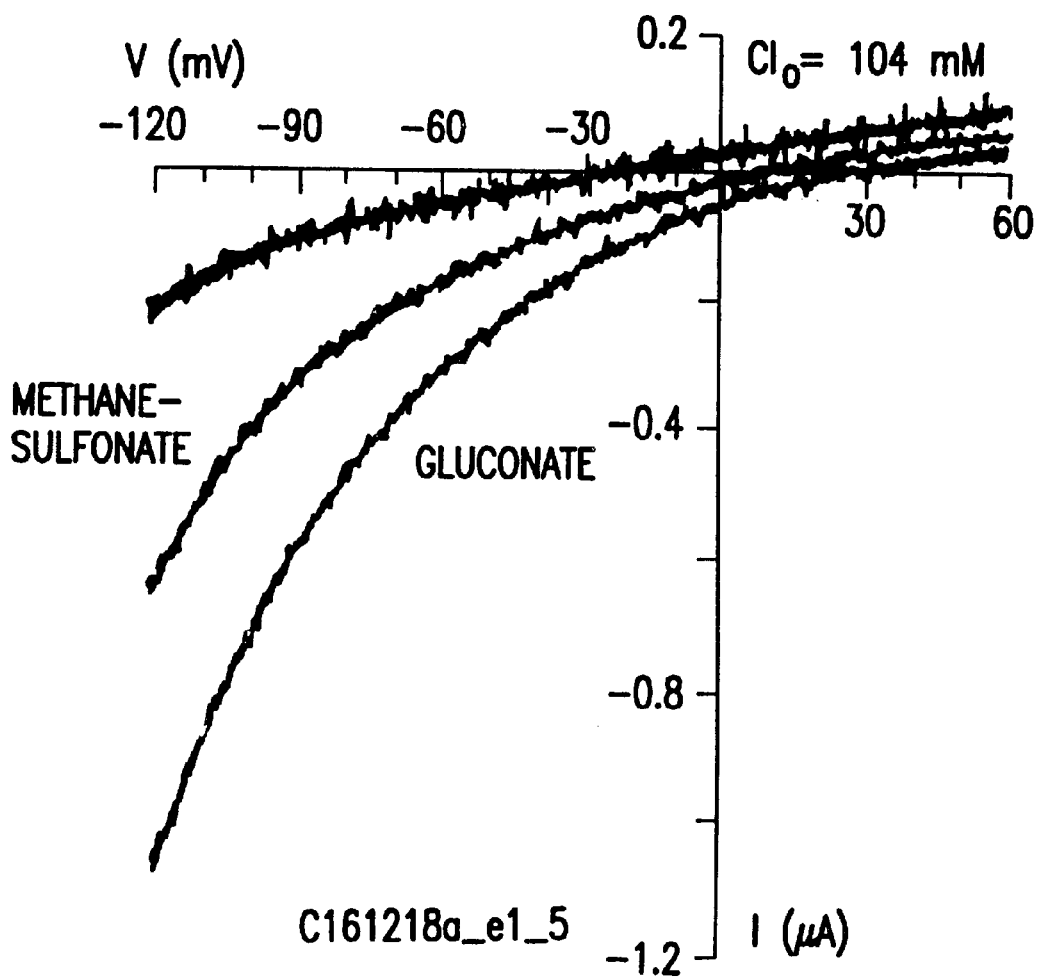
FIG. 6 shows that the CfGluCl-1 channel is selective for chloride.

FIG. 6 shows that the CfGluCl-1 channel is selective for chloride. Each curve represents the difference between the current measured with and without 10 μM glutamate. The voltage was ramped from –120 to +60 mV at 1 volt/second. Chloride concentration was reduced from 104 mM to 8.2 mM by equimolar substitution of NaCl by Na-methanesulfonate or Na-gluconate. Each current-voltage relationship was fit to a seventh order polynomial using non-linear least squares analysis and the reversal potential was taken as the x-intercept of this polynomial. The reversal potential measurements indicate that the relative permeability for methanesulfonate ( i.e., (permeability for methanesulfonate)l (permeability for chloride)) is 0.218 and the relative permeability for gluconate is 0.064.

Figure 7A:
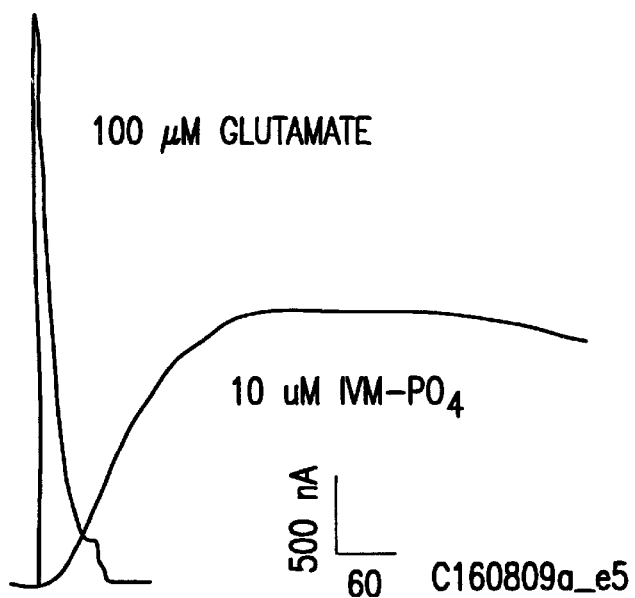
FIGS. 7A and 7B show that ivermectin phosphate (IVM-PO$_4$) is an agonist of the C. felis GluCl channel encoded by CfGluCl-1.
Figure 7B:
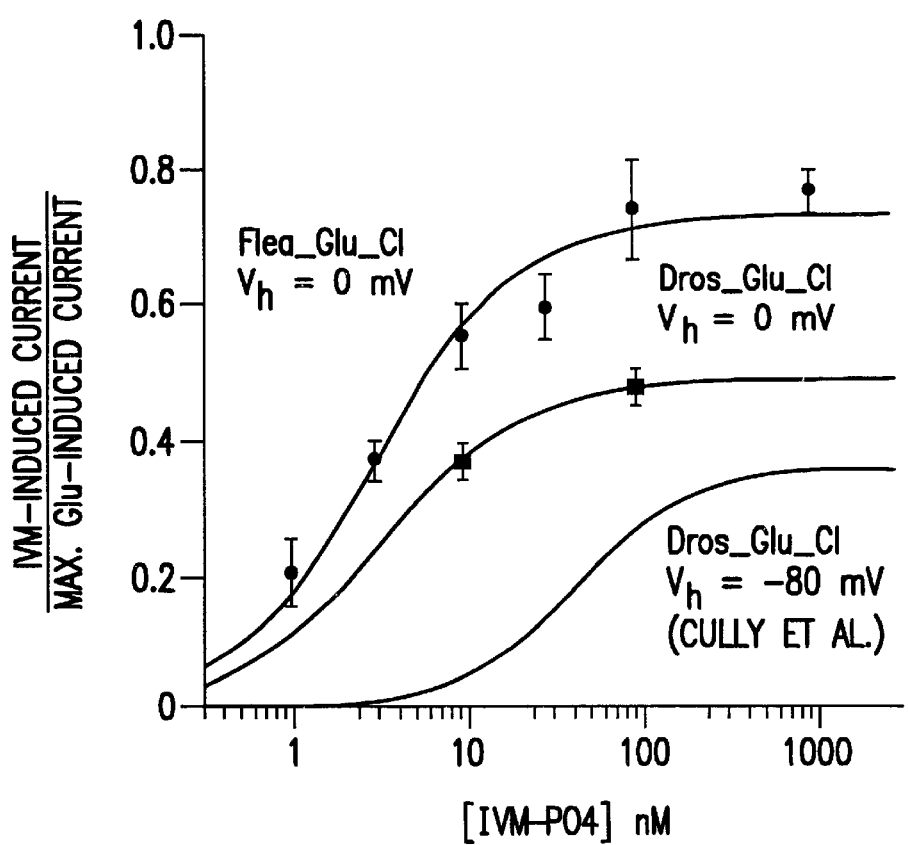

FIGS. 7A and B show that ivermectin phosphate is an agonist of the flea GluCl channel encoded by CfGluCl-1. FIG. 7A shows activation of CfGluCl-1 by ivermectin phosphate (IVM-PO$_4$) and superimposed current recordings showing activation by 100 μM glutamate and 10 nM IVM-PO$_4$. The activation by IVM-PO$_4$ has a sigmoidal onset suggesting that multiple binding sites must be occupied for opening. FIG. 7B shows the concentration-response curve for IVM-PO$_4$. A single [IVM-PO$_4$] was tested on each oocyte. The ordinate is the maximal current induced by IVM-PO$_4$ normalized by the peak current induced by 100 μM glutamate, a maximally effective concentration. The error bars indicate ±S.E.M. The holding potential was 0 mV for both sets of measurements. The filled circles represent data for CfGluCl-1. The solid curve is the best fit to this data by (1) $I = I_{ivm,max}/\{1+(EC_{50}/[\text{IVM-PO}_4])^n\}$ where $I_{ivm,max}=0.718$, $EC_{50}=2.93$ nM, and n=1.0. Also shown is the dose-response curve previously reported for the DmGluCl1 clone from *Drosophila metanogaster*, except that in these earlier studies the holding potential was –80 mV (Cully et al., J. 1996, *J. Biol. Chem.* 271: 20187–20191). This curve is the best fit to equation (1) for modification by IVM-PO$_4$, where $I_{ivm,max}=0.35$, $EC_{50}=41$ nM, and n=1.2. This data shows a 10-fold increase in potency. Additional data shows that this increase in potency is not the result of differences between the clones and/or in measurement technique. The measurements were repeated on DmGluCl1 at a holding potential of 0 mV (filled squares); the solid curve is the best fit to equation (1) with the constraint that the $EC_{50}$ and n are the same as for CfGluCl1. The goodness of fit indicates that the $EC_{50}$ for DmGluCl1 is similar to that for CfGluCl1 and that both channels are activated by WM-PO$_4$ at concentrations 10-fold lower than previously recognized.

SEQUENCE LISTING

<160> NUMBER OF SEQ ID NOS: 8

<210> SEQ ID NO 1
<211> LENGTH: 1368
<212> TYPE: DNA
<213> ORGANISM: ctenocephalides felis

<400> SEQUENCE: 1

-continued

```
atggacagca ttagtttgct cctacttttg ataacatgtc taagtctaca cacatgctta      60
tctgcaaatg caaaacctcg tctaggaggc ggcaaagaaa atttcagggc caaagaaaag     120
caagttctgg accaaatttt aggcccaggc cattacgatg ccagaataag gccttctgga     180
gtcaatggaa ctggagacgg tccgaccgtg gtagcagtca acatctatct gagatcaatc     240
agcgaaatag atgactacaa atggaatac agtgtccagt taactttcag ggaacaatgg      300
caggatgaga ggttgaaatt taacgacttt ggaggtcgtt taaatactt aacactaacc      360
gaagcaagtc gtgtatggat gcccgatttg ttctttgcga atgaaaagga gggccacttt     420
cacaacatca tcatgccgaa cgtctacatt cgtattttc cttacggttc cgtactatac      480
agcatcagga tatcgcttac tttggcgtgt cctatgaatc tgaaactgta tccgctcgat     540
aggcaggtgt gctctctccg gatggccagt tatggttgga ccacaaacga tctggtgttt     600
ttgtggaagg aaggtgaccc ggtgcaggtt gtcaagaatc tacatctgcc caggtttacg     660
ttggagaagt tcttgacgga ttattgtaac agcaaaacca ataccggtga atacagttgc     720
ctgaaggtcg acctgctctt taaacgagag ttctcgtact acctgatcca gatctacatt     780
ccttgttgca tgttggtgat cgtttcctgg gtgtcgttct ggttggacca gggagcggtt     840
ccggccagag tatcactggg tgtgaccact ctcctcacca tggccaccca gacgtcgggc     900
ataaacgcct ccctgccgcc agtgtcctac acaaaagcca tcgacgtctg gaccggagtc     960
tgcctcacgt tcgtcttcgg ggctttgctc gaattcgccc tcgtcaacta cgcctccaga    1020
tccgatatgc acagggaaaa catgaagaaa agcgcagggg aacttgaaca agcagccagc    1080
ctggacgccg cctccgacct gatggacggc actgatggca cttttgctat gaagcctctg    1140
gtacgccact ccgtcgacgc cgtcggtctc gataaggttc gtcagtgcga gatacacatg    1200
cagccggcgt ccaggcagaa ctgctgcagg agctggataa gcaaattccc gacgaggtcg    1260
aaacgcatcg acgtcatatc aagaatcact ttcccgctgg tgtttgcttt gttcaatctg    1320
gtgtactggt cgacctattt gttcagggac gaggcggagg agaattag                 1368
```

<210> SEQ ID NO 2
<211> LENGTH: 455
<212> TYPE: PRT
<213> ORGANISM: ctenocephalides felis

<400> SEQUENCE: 2

```
Met Asp Ser Ile Ser Leu Leu Leu Leu Ile Thr Cys Leu Ser Leu
 1               5                  10                  15

His Thr Cys Leu Ser Ala Asn Ala Lys Pro Arg Leu Gly Gly Gly Lys
                20                  25                  30

Glu Asn Phe Arg Ala Lys Glu Lys Gln Val Leu Asp Gln Ile Leu Gly
            35                  40                  45

Pro Gly His Tyr Asp Ala Arg Ile Arg Pro Ser Gly Val Asn Gly Thr
        50                  55                  60

Gly Asp Gly Pro Thr Val Val Ala Val Asn Ile Tyr Leu Arg Ser Ile
    65                  70                  75                  80

Ser Glu Ile Asp Asp Tyr Lys Met Glu Tyr Ser Val Gln Leu Thr Phe
                85                  90                  95

Arg Glu Gln Trp Gln Asp Glu Arg Leu Lys Phe Asn Asp Phe Gly Gly
            100                 105                 110

Arg Leu Lys Tyr Leu Thr Leu Thr Glu Ala Ser Arg Val Trp Met Pro
        115                 120                 125
```

```
Asp Leu Phe Phe Ala Asn Glu Lys Glu Gly His Phe His Asn Ile Ile
    130                 135                 140

Met Pro Asn Val Tyr Ile Arg Ile Phe Pro Tyr Gly Ser Val Leu Tyr
145                 150                 155                 160

Ser Ile Arg Ile Ser Leu Thr Leu Ala Cys Pro Met Asn Leu Lys Leu
                165                 170                 175

Tyr Pro Leu Asp Arg Gln Val Cys Ser Leu Arg Met Ala Ser Tyr Gly
            180                 185                 190

Trp Thr Thr Asn Asp Leu Val Phe Leu Trp Lys Glu Gly Asp Pro Val
        195                 200                 205

Gln Val Val Lys Asn Leu His Leu Pro Arg Phe Thr Leu Glu Lys Phe
    210                 215                 220

Leu Thr Asp Tyr Cys Asn Ser Lys Thr Asn Thr Gly Glu Tyr Ser Cys
225                 230                 235                 240

Leu Lys Val Asp Leu Leu Phe Lys Arg Glu Phe Ser Tyr Tyr Leu Ile
                245                 250                 255

Gln Ile Tyr Ile Pro Cys Cys Met Leu Val Ile Val Ser Trp Val Ser
            260                 265                 270

Phe Trp Leu Asp Gln Gly Ala Val Pro Ala Arg Val Ser Leu Gly Val
        275                 280                 285

Thr Thr Leu Leu Thr Met Ala Thr Gln Thr Ser Gly Ile Asn Ala Ser
    290                 295                 300

Leu Pro Pro Val Ser Tyr Thr Lys Ala Ile Asp Val Trp Thr Gly Val
305                 310                 315                 320

Cys Leu Thr Phe Val Phe Gly Ala Leu Leu Glu Phe Ala Leu Val Asn
                325                 330                 335

Tyr Ala Ser Arg Ser Asp Met His Arg Glu Asn Met Lys Lys Lys Arg
            340                 345                 350

Arg Glu Leu Glu Gln Ala Ala Ser Leu Asp Ala Ala Ser Asp Leu Met
        355                 360                 365

Asp Gly Thr Asp Gly Thr Phe Ala Met Lys Pro Leu Val Arg His Ser
    370                 375                 380

Val Asp Ala Val Gly Leu Asp Lys Val Arg Gln Cys Glu Ile His Met
385                 390                 395                 400

Gln Pro Ala Ser Arg Gln Asn Cys Cys Arg Ser Trp Ile Ser Lys Phe
                405                 410                 415

Pro Thr Arg Ser Lys Arg Ile Asp Val Ile Ser Arg Ile Thr Phe Pro
            420                 425                 430

Leu Val Phe Ala Leu Phe Asn Leu Val Tyr Trp Ser Thr Tyr Leu Phe
        435                 440                 445

Arg Asp Glu Ala Glu Glu Asn
    450                 455

<210> SEQ ID NO 3
<211> LENGTH: 1297
<212> TYPE: DNA
<213> ORGANISM: ctenocephalides felis

<400> SEQUENCE: 3
atggacagca ttagtttgct cctactttg ataacatgtc taagtctaca cacatgctta      60
tctgcaaatg caaaacctcg tctaggaggc ggcaaagaaa atttcagggc caagaaaag     120 caagttctgg accaaatttt aggcccaggc cattacgatg ccagaataag gccttctgga    180
gtcaatggaa ctggaataca gtgtccagtt aactttcagg gaacaatggc aggatgagag    240
```

```
gttgaaattt aacgactttg gaggtcgttt aaaatactta acactaaccg aagcaagtcg      300
tgtatggatg cccgatttgt tctttgcgaa tgaaaggag ggccactttc acaacatcat       360
catgccgaac gtctacattc gtattttccc ttacggttcc gtactataca gcatcaggat      420
atcgcttact ttggcgtgtc ctatgaatct gaaactgtat ccgctcgata ggcaggtgtg      480
ctctctccgg atggccagtt atggttggac cacaaacgat ctggtgtttt tgtggaagga      540
aggtgacccg gtgcaggttg tcaagaatct acatctgccc aggtttacgt tggagaagtt      600
cttgacggat tattgtaaca gcaaaaccaa taccggtgaa tacagttgcc tgaaggtcga      660
cctgctcttt aaacgagagt tctcgtacta cctgatccag atctacattc cttgttgcat      720
gttggtgatc gtttcctggg tgtcgttctg gttggaccag ggagcggttc cggccagagt      780
atcactgggt gtgaccactc tcctcaccat ggccacccag acgtcgggca taaacgcctc      840
cctgccgcca gtgtcctaca caaaagccat cgacgtctgg accggagtct gcctcacgtt      900
cgtcttcggg gctttgctcg aattcgccct cgtcaactac gcctccagat ccgatatgca      960
cagggaaaac atgaagaaaa agcgcaggga acttgaacaa gcagccagcc tggacgccgc     1020
ctccgacctg atggacggca ctgatggcac ttttgctatg aagcctctgg tacgccactc     1080
cgtcgacgcc gtcggtctcg ataaggttcg tcagtgcgag atacacatgc agccggcgtc     1140
caggcagaac tgctgcagga gctggataag caaattcccg acgaggtcga aacgcatcga     1200
cgtcatatca agaatcactt tcccgctggt gtttgctttg ttcaatctgg tgtactggtc     1260
gacctatttg ttcagggacg aggcggagga gaattag                              1297

<210> SEQ ID NO 4
<211> LENGTH: 78
<212> TYPE: PRT
<213> ORGANISM: ctenocephalides felis

<400> SEQUENCE: 4

Met Asp Ser Ile Ser Leu Leu Leu Leu Ile Thr Cys Leu Ser Leu
 1               5                  10                  15

His Thr Cys Leu Ser Ala Asn Ala Lys Pro Arg Leu Gly Gly Gly Lys
            20                  25                  30

Glu Asn Phe Arg Ala Lys Glu Lys Gln Val Leu Asp Gln Ile Leu Gly
        35                  40                  45

Pro Gly His Tyr Asp Ala Arg Ile Arg Pro Ser Gly Val Asn Gly Thr
    50                  55                  60

Gly Ile Gln Cys Pro Val Asn Phe Gln Gly Thr Met Ala Gly
65                  70                  75

<210> SEQ ID NO 5
<211> LENGTH: 21
<212> TYPE: DNA
<213> ORGANISM: Artificial Sequence
<220> FEATURE:
<223> OTHER INFORMATION: oligonucleotide

<400> SEQUENCE: 5
ctcagagtca ggatccggct a                                                21

<210> SEQ ID NO 6
<211> LENGTH: 21
<212> TYPE: DNA
<213> ORGANISM: Artificial Sequence
<220> FEATURE:
<223> OTHER INFORMATION: oligonucleotide
```

<400> SEQUENCE: 6
ctgaaagtta actggacact g                                              21

<210> SEQ ID NO 7
<211> LENGTH: 751
<212> TYPE: DNA
<213> ORGANISM: ctenocephalides felis

<400> SEQUENCE: 7
aactagtgga tcccccgggc tgcaggattc ggcacgagaa ttttttaaaa taatcctcaa     60
cagcatgata caagaggatg attttatgat ccctgtaaac acttgcttga attttagatt    120
gcaactggag gctccgctga cactctctct tgttcgagca caggaattgc tcgacatctg    180
gtcaaacgcg ggctacttca taatatccga cgatgacaat ttaatgttcg gagcaagaac    240
aattgcagaa tttgaagtgt actttaacga tacattcgaa ggacgcatga aaatgtgcac    300
gatgtgcatg ttgcccacct tctattgacc agcaagcacc cttcgccgg tgagcatgtc     360 acccaccgac aggcgcctcc tgtgcgccct cgacgacctg cacttagcgg ttgctaagaa    420
gccctaagaa gccgagacgg ttcgcttcgc ccggggcga ttcctcacga tgcacaagcg     480
gaggcgcaag aggctgacga cgaggagcct cagagtcagg atccggctat attggacgat    540
atgctgcatg gtccctgtca tacaaatact ccttcgcctt cactggaacc aaccaagact    600
gtccccacgt gtccgacatc agttgaagga aattctgtga cgacatggca acactttgt    660 tcaggaacaa caataacatc atcgacacag aatatcggcg aagcctattc ttcgattcaa    720
gaagaagaat tcttcacttt tatcttcagg g                                   751

<210> SEQ ID NO 8
<211> LENGTH: 532
<212> TYPE: DNA
<213> ORGANISM: ctenocephalides felis

<400> SEQUENCE: 8
tcagagtcag gatccggcta tattggacga tatgctgcat ggtccctgtc atacaaatac    60
tccttcgcct tcactggaac caaccaagac tgtccccacg tgtccgacat cagttgaagg    120
aaattctgtg acgacatggc aacacttttg ttcaggaaca acaataacat catcgacaca    180
gaatatcggc gaagcctatt cttcgattca agaagaagaa tttcttcact ttatcttcag    240
ggatggacag cattagtttg ctcctacttt tgataacatg tctaagtcta cacacatgct    300
tatctgcaaa tgcaaaacct cgtctaggag gcggcaaaga aatttcagg gccaaagaaa     360 agcaagttct ggaccaaatt ttaggcccag gccattacga tgccagaata aggccttctg    420
gagtcaatgg aactggagac ggtccgaccg tggtagcagt caacatctat ctgagatcaa    480
tcagcgaaat agatgactac aaaatggaat acagtgtcca gttaactttc ag            532

What is claimed:

1. A purified DNA molecule encoding a *C. felis* GluCl channel protein wherein said protein comprises the amino acid sequence as follows:

| | | |
|---|---|---|
| MDSISLLLLL | ITCLSLHTCL | SANAKPRLGG GKENFRAKEK |
| QVLDQILGPG | HYDARIRPSG | VNGTGDGPTV VAVNIYLRSI |
| SEIDDYKMEY | SVQLTFREQW | QDERLKFNDF GGRLKYLTLT |
| EASRVWMPDL | FFANEKEGHF | HNIIMPNVYI RIFPYGSVLY |
| SIRISLTLAC | PMNLKLYPLD | RQVCSLRMAS YGWTTNDLVF |
| LWKEGDPVQV | VKNLHLPRFT | LEKFLTDYCN SKTNTGEYSC |
| LKVDLLFKRE | FSYYLIQIYI | PCCMLVIVSW VSFWLDQGAV |
| PARVSLGVTT | LLTMATQTSG | INASLPPVSY TKAIDVWTGV |
| CLTFVFGALL | EFALVNYASR | SDMHRENMKK KRRELEQAAS |
| LDAASDLMDG | TDGTFAMKPL | VRHSVDAVGL DKVRQCEIHM |
| QPASRQNCCR | SWISKFPTRS | KRIDVISRIT FPLVFALFNL |
| VYWSTYLFRD | EAEEN, | | as set forth in three-letter abbreviation in SEQ ID NO:2.

2. An expression vector for expressing a *C. felis* GluCl channel protein in a recombinant host cell wherein said expression vector comprises a DNA molecule of claim 1.

3. A host cell which expresses a recombinant *C. felis* GluCl channel protein wherein said host cell contains the expression vector of claim 2.

4. A process for expressing a *C. felis* GluCl channel protein in a recombinant host cell, comprising:
   (a) transfecting the expression vector of claim 2 into a suitable host cell; and,
   (b) culturing the host cells of step (a) under conditions which allow expression of said *C. felis* GluCl channel protein from said expression vector.

5. A purified DNA molecule encoding a *C. felis* GluCl channel protein wherein said protein consists of the amino acid sequence as follows:

| | | |
|---|---|---|
| MDSISLLLLL | ITCLSLHTCL | SANAKPRLGG GKENFRAKEK |
| QVLDQILGPG | HYDARIRPSG | VNGTGDGPTV VAVNIYLRSI |
| SEIDDYKMEY | SVQLTFREQW | QDERLKFNDF GGRLKYLTLT |
| EASRVWMPDL | FFANEKEGHF | HNIIMPNVYI RIFPYGSVLY |
| SIRISLTLAC | PMNLKLYPLD | RQVCSLRMAS YGWTTNDLVF |
| LWKEGDPVQV | VKNLHLPRFT | LEKFLTDYCN SKTNTGEYSC |
| LKVDLLFKRE | FSYYLIQIYI | PCCMLVIVSW VSFWLDQGAV |
| PARVSLGVTT | LLTMATQTSG | INASLPPVSY TKAIDVWTGV |
| CLTFVFGALL | EFALVNYASR | SDMHRENMKK KRRELEQAAS |
| LDAASDLMDG | TDGTFAMKPL | VRHSVDAVGL DKVRQCEIHM |
| QPASRQNCCR | SWISKFPTRS | KRIDVISRIT FPLVFALFNL |
| VYWSTYLFRD | EAEEN, | | as set forth in three-letter abbreviation in SEQ ID NO:2.

6. An expression vector for expressing a *C. felis* GluCl channel protein in a recombinant host cell wherein said expression vector comprises a DNA molecule of claim 5.

7. A host cell which expresses a recombinant *C. felis* GluCl channel protein wherein said host cell contains the expression vector of claim 6.

8. A process for expressing a *C. felis* GluCl channel protein in a recombinant host cell, comprising:
   (a) transfecting the expression vector of claim 6 into a suitable host cell; and,
   (b) culturing the host cells of step (a) under conditions which allow expression of said *C. felis* GluCl channel protein from said expression vector.

9. A purified DNA molecule encoding a recombinant C. felis GluCl channel protein wherein said DNA molecule comprises the nucleotide sequence as set forth in SEQ ID NO:1, as follows:

| | | | | |
|---|---|---|---|---|
| ATGGACAGCA | TTAGTTTGCT | CCTACTTTTG | ATAACATGTC | TAAGTCTACA |
| CACATGCTTA | TCTGCAAATG | CAAAACCTCG | TCTAGGAGGC | GGCAAAGAAA |
| ATTTCAGGGC | CAAAGAAAAG | CAAGTTCTGG | ACCAAATTTT | AGGCCCAGGC |
| CATTACGATG | CCAGAATAAG | GCCTTCTGGA | GTCAATGGAA | CTGGAGACGG |
| TCCGACCGTG | GTAGCAGTCA | ACATCTATCT | GAGATCAATC | AGCGAAATAG |
| ATGACTACAA | AATGGAATAC | AGTGTCCAGT | TAACTTTCAG | GGAACAATGG |
| CAGGATGAGA | GGTTGAAATT | TAACGACTTT | GGAGGTCGTT | TAAAATACTT |
| AACACTAACC | GAAGCAAGTC | GTGTATGGAT | GCCCGATTTG | TTCTTTGCGA |
| ATGAAAAGGA | GGGCCACTTT | CACAACATCA | TCATGCCGAA | CGTCTACATT |
| CGTATTTTTC | CTTACGGTTC | CGTACTATAC | AGCATCAGGA | TATCGCTTAC |

-continued

```
TTTGGCGTGT CCTATGAATC TGAAACTGTA TCCGCTCGAT AGGCAGGTGT

GCTCTCTCCG GATGGCCAGT TATGGTTGGA CCACAAACGA TCTGGTGTTT

TTGTGGAAGG AAGGTGACCC GGTGCAGGTT GTCAAGAATC TACATCTGCC

CAGGTTTACG TTGGAGAAGT TCTTGACGGA TTATTGTAAC AGCAAAACCA

ATACCGGTGA ATACAGTTGC CTGAAGGTCG ACCTGCTCTT TAAACGAGAG

TTCTCGTACT ACCTGATCCA GATCTACATT CCTTGTTGCA TGTTGGTGAT

CGTTTCCTGG GTGTCGTTCT GGTTGGACCA GGGAGCGGTT CCGGCCAGAG

TATCACTGGG TGTGACCACT CTCCTCACCA TGGCCACCCA GACGTCGGGC

ATAAACGCCT CCCTGCCGCC AGTGTCCTAC ACAAAAGCCA TCGACGTCTG

GACCGGAGTC TGCCTCACGT TCGTCTTCGG GGCTTTGCTC GAATTCGCCC

TCGTCAACTA CGCCTCCAGA TCCGATATGC ACAGGGAAAA CATGAAGAAA

AAGCGCAGGG AACTTGAACA AGCAGCCAGC CTGGACGCCG CCTCCGACCT

GATGGACGGC ACTGATGGCA CTTTTGCTAT GAAGCCTCTG GTACGCCACT

CCGTCGACGC CGTCGGTCTC GATAAGGTTC GTCAGTGCGA GATACACATG

CAGCCGGCGT CCAGGCAGAA CTGCTGCAGG AGCTGGATAA GCAAATTCCC

GACGAGGTCG AAACGCATCG ACGTCATATC AAGAATCACT TTCCCGCTGG

TGTTTGCTTT GTTCAATCTG GTGTACTGGT CGACCTATTT GTTCAGGGAC

GAGGCGGAGG AGAATTAG, (SEQ ID NO:1).
```

10. An expression vector for expressing a recombinant *C. felis* GluCl channel protein wherein said expression vector comprises a DNA molecule of claim 9.

11. A host cell which expresses a recombinant recombinant *C. felis* GluCl channel protein wherein said host cell contains the expression vector of claim 10.

12. A process for expressing a recombinant *C. felis* GluCl channel protein in a recombinant host cell, comprising:

(a) transfecting the expression vector of claim 10 into a suitable host cell; and, (b) culturing the host cells of step (a) under conditions which allow expression of said recombinant *C. felis* GluCl channel protein from said expression vector.

13. A purified DNA molecule encoding a recombinant *C. felis* GluCl channel protein wherein said DNA molecule consists of the peptide sequence as set forth in SEQ ED NO:1, as follows:

```
ATGGACAGCA TTAGTTTGCT CCTACTTTTG ATAACATGTC TAAGTCTACA

CACATGCTTA TCTGCAAATG CAAAACCTCG TCTAGGAGGC GGCAAAGAAA

ATTTCAGGGC CAAAGAAAAG CAAGTTCTGG ACCAAATTTT AGGCCCAGGC

CATTACGATG CCAGAATAAG GCCTTCTGGA GTCAATGGAA CTGGAGACGG

TCCGACCGTG GTAGCAGTCA ACATCTATCT GAGATCAATC AGCGAAATAG

ATGACTACAA AATGGAATAC AGTGTCCAGT TAACTTTCAG GGAACAATGG

CAGGATGAGA GGTTGAAATT TAACGACTTT GGAGGTCGTT TAAAATACTT

AACACTAACC GAAGCAAGTC GTGTATGGAT GCCCGATTTG TTCTTTGCGA

ATGAAAAGGA GGGCCACTTT CACAACATCA TCATGCCGAA CGTCTACATT

CGTATTTTTC CTTACGGTTC CGTACTATAC AGCATCAGGA TATCGCTTAC

TTTGGCGTGT CCTATGAATC TGAAACTGTA TCCGCTCGAT AGGCAGGTGT
```

```
GCTCTCTCCG GATGGCCAGT TATGGTTGGA CCACAAACGA TCTGGTGTTT

TTGTGGAAGG AAGGTGACCC GGTGCAGGTT GTCAAGAATC TACATCTGCC

CAGGTTTACG TTGGAGAAGT TCTTGACGGA TTATTGTAAC AGCAAAACCA

ATACCGGTGA ATACAGTTGC CTGAAGGTCG ACCTGCTCTT TAAACGAGAG

TTCTCGTACT ACCTGATCCA GATCTACATT CCTTGTTGCA TGTTGGTGAT

CGTTTCCTGG GTGTCGTTCT GGTTGGACCA GGGAGCGGTT CCGGCCAGAG

TATCACTGGG TGTGACCACT CTCCTCACCA TGGCCACCCA GACGTCGGGC.

ATAAACGCCT CCCTGCCGCC AGTGTCCTAC ACAAAAGCCA TCGACGTCTG

GACCGGAGTC TGCCTCACGT TCGTCTTCGG GGCTTTGCTC GAATTCGCCC

TCGTCAACTA CGCCTCCAGA TCCGATATGC ACAGGGAAAA CATGAAGAAA

AAGCGCAGGG AACTTGAACA AGCAGCCAGC CTGGACGCCG CCTCCGACCT

GATGGACGGC ACTGATGGCA CTTTTGCTAT GAAGCCTCTG GTACGCCACT

CCGTCGACGC CGTCGGTCTC QATAAGGTTC GTCAGTGCGA GATACACATG

CAGCCGGCGT CCAGGCAGAA CTGCTGCAGG AGCTGGATAA GCAAATTCCC

GACGAGGTCG AAACGCATCG ACGTCATATC AAQAATCACT TTCCCGCTGG

TGTTTGCTTT GTTCAATCTG GTGTACTGGT CGACCTATTT GTTCAGGGAC

GAGGCGGAGG AGAATTAG, (SEQ ID NO:1).
```

14. An expression vector for expressing a recombinant *C. felis* GluCl channel protein wherein said expression vector comprises a DNA molecule of claim 13.

15. A host cell which expresses a recombinant recombinant *C. felis* GluCl channel protein wherein said host cell contains the expression vector of claim 14.

16. A process for expressing a recombinant *C. felis* GluCl channel protein in a recombinant host cell, comprising:
   (a) transfecting the expression vector of claim 14 into a suitable host cell; and,
   (b) culturing the host cells of step (a) under conditions which allow expression of said recombinant *C. felis* GluCl channel protein from said expression vector.

17. A purified DNA molecule encoding a truncated portion of a *C. felis* GluCl channel protein wherein said protein consists of the amino acid sequence as follows:

as set forth in three-letter abbreviation in SEQ ID NO:4.

18. An expression vector for expressing a *C. felis* GluCl channel protein in a recombinant host cell wherein said expression vector comprises a DNA molecule of claim 17.

19. A host cell which expresses a recombinant *C. felis* GluCl channel protein wherein said host cell contains the expression vector of claim 18.

20. A process for expressing a *C. felis* GluCl channel protein in a recombinant host cell, comprising:
   (a) transfecting the expression vector of claim 18 into a suitable host cell; and,
   (b) culturing the host cells of step (a) under conditions which allow expression of said *C. felis* GluCl channel protein from said expression vector.

21. A purified DNA molecule encoding a recombinant *C. felis* GluCl channel protein wherein said DNA molecule consists of the nucleotide sequence as set forth in SEQ ID NO:3, as follows:

```
MDSISLLLLL ITCLSLHTCL SANAKPRLGG GKENFRAKEK QVLDQILGPG

HYDARIRPSG VNGTGIQCPV NFQGTMAG,
```

```
ATGGACAGCA TTAGTTTGCT CCTACTTTTG ATAACATGTC TAAGTCTACA
CACATGCTTA TCTGCAAATG CAAAACCTCG TCTAGGAGGC GGCAAAGAAA
ATTTCAGGGC CAAAGAAAAG CAAGTTCTGG ACCAAATTTT AGGCCCAGGC
CATTACGATG CCAGAATAAG GCCTTCTGGA GTCAATGGAA CTGGAATACA
GTGTCCAGTT AACTTTCAGG GAACAATGGC AGGATGAGAG GTTGAAATTT
AACGACTTTG GAGGTCGTTT AAAATACTTA ACACTAACCG AAGCAAGTCG
TGTATGGATG CCCGATTTGT TCTTTGCGAA TGAAAAGGAG GGCCACTTTC
ACAACATCAT CATGCCGAAC GTCTACATTC GTATTTTTCC TTACGGTTCC
GTACTATACA GCATCAGGAT ATCGCTTACT TTGGCGTGTC CTATGAATCT
GAAACTGTAT CCGCTCGATA GGCAGGTGTG CTCTCTCCGG ATGGCCAGTT
ATGGTTGGAC CACAAACGAT CTGGTGTTTT TGTGGAAGGA AGGTGACCCG
GTGCAGGTTG TCAAGAATCT ACATCTGCCC AGGTTTACGT TGGAGAAGTT
CTTGACGGAT TATTGTAACA GCAAAACCAA TACCGGTGAA TACAGTTGCC
TGAAGGTCGA CCTGCTCTTT AAACGAGAGT TCTCGTACTA CCTGATCCAG
ATCTACATTC CTTGTTGCAT GTTGGTGATC GTTTCCTGGG TGTCGTTCTG
GTTGGACCAG GGAGCGGTTC CGGCCAGAGT ATCACTGGGT GTGACCACTC
TCCTCACCAT GGCCACCCAG ACGTCGGGCA TAAACGCCTC CCTGCCGCCA
GTGTCCTACA CAAAAGCCAT CGACGTCTGG ACCGGAGTCT GCCTCACGTT
CGTCTTCGGG GCTTTGCTCG AATTCGCCCT CGTCAACTAC GCCTCCAGAT
CCGATATGCA CAGGGAAAAC ATGAAGAAAA AGCGCAGGGA ACTTGAACAA
GCAGCCAGCC TGGACGCCGC CTCCGACCTG ATGGACGGCA CTGATGGCAC
TTTTGCTATG AAGCCTCTGG TACGCCACTC CGTCGACGCC GTCGGTCTCG
ATAAGGTTCG TCAGTGCGAG ATACACATGC AGCCGGCGTC CAGGCAGAAC
TGCTGCAGGA GCTGGATAAG CAAATTCCCG ACGAGGTCGA AACGCATCGA
CGTCATATCA AGAATCACTT TCCCGCTGGT GTTTGCTTTG TTCAATCTGG
TGTACTGGTC GACCTATTTG TTCAGGGACG AGGCGGAGGA GAATTAG,
(SEQ ID NO:3).
```

22. An expression vector for expressing a recombinant *C. felis* GluCl channel protein wherein said expression vector comprises a DNA molecule of claim 21.

23. A host cell which expresses a recombinant *C. felis* GluCl channel protein wherein said host cell contains the expression vector of claim 22.

24. A process for expressing a recombinant *C. felis* GluCl channel protein in a recombinant host cell, comprising:

(a) transfecting the expression vector of claim 22 into a suitable host cell; and, (b) culturing the host cells of step (a) under conditions which allow expression of said recombinant *C. felis* GluCl channel protein from said expression vector.

* * * * *

UNITED STATES PATENT AND TRADEMARK OFFICE
CERTIFICATE OF CORRECTION

PATENT NO.   : 6,358,701 B1
DATED         : March 19, 2002
INVENTOR(S)  : Warmke, Jeffrey W. et al.

It is certified that error appears in the above-identified patent and that said Letters Patent is hereby corrected as shown below:

Column 39,
Line 31, replace "DNA molecule of claim 1" with -- contiguous DNA sequence encoding said protein, wherein said protein comprises the amino acid sequence of SEQ ID NO:2 --.
Line 44, replace "A" with -- The --;
Lines 44-45, replace "encoding a *C. felis* GluCl channel protein" with -- of claim 1 --;
Line 46, replace "as follows: MDSISLLLLL ITCLSLHTCL SANAKPRLGG GKENFRAKEK QVLDQILGPG HYDARIRPSG VNGTGDGPTV VAVNIYLRSI SEIDDYKMEY SVQLTFREQW QDERLKFNDF GGRLKYLTLT EASRVWMPDL FFANEKEGHF HNIIMPNVYI RIFPYGSVLY SIRISLTLAC PMNLKLYPLD RQVCSLRMAS YGWTTNDLVF LWKEGDPVQV VKNLHLPRFT LEKFLTDYCN SKTNTGEYSC LKVDLLFKRE FSYYLIQIYI PCCMLVIVSW VSFWLDQGAV PARVSLGVTT LLTMATQTSG INASLPPVSY TKAIDVWTGV CLTFVFGALL EFALVNYASR SDMHRENMKK KRRELEQAAS LDAASDLMDG TDGTFAMKPL VRHSVDAVGL DKVRQCHEIHM QPASRQNCCRSWISKFPTRS KRIDVISRIT FPLVFALFNL VYWSTYLFRD EAEEN, as set forth in three letter abbreviation in" with -- of --.

Column 40,
Line 26, replace "A" with -- The --;
Lines 26-28, delete "for expressing a *C. felis* GluCl channel protein in a recombinant host cell wherein said expression vector comprises a DNA molecule";
Line 28, replace "5" with -- 2, wherein said protein consists of the amino acid sequence of SEQ ID NO:2. --
Lines 42-43, replace "C. felis" with -- *C. felis* --.

Column 41,
Line 38, replace "of claim 9" with -- comprising the sequence of SEQ ID NO:1 --.
Line 40, delete the second occurrence of the "recombinant".

Column 42,
Line 42, replace "A pruified" with -- The --
Lines 42-43, delete "encoding a recombinant *C. felis* GluCl channel protein" with -- of claim 9 --;
Line 44, replace "peptide" with -- nucleotide -- and "SEQ ED" with -- SEQ ID --.

UNITED STATES PATENT AND TRADEMARK OFFICE
CERTIFICATE OF CORRECTION

PATENT NO. : 6,358,701 B1
DATED : March 19, 2002
INVENTOR(S) : Warmke, Jeffrey W. et al.

It is certified that error appears in the above-identified patent and that said Letters Patent is hereby corrected as shown below:

Column 43,
Line 35, replace "An" with -- The --;
Lines 35-37, replace "for expressing a recombinant *C. Felis* GluCl channel protein wherein said expression vector comprises a" with -- of claim 10, wherein said --;
Line 37, replace "of claim 13" with -- consists of the sequence of SEQ ID NO:1 --.
Lines 39-40, delete the second occurrence of "recombinant".
Line 51, insert -- comprising a contiguous sequence -- after the term "DNA molecule" and before the word "encoding";
Line 52, replace "aC. Felis" with -- a *C. felis* --.

Column 44,
Line 38, replace "DNA molecule of claim 17" with -- contiguous DNA sequence encoding the amino acid sequence of SEQ ID NO: 4. --.

Column 45,
Line 50, replace "of claim 21" with -- consisting of the sequence of SEQ ID NO:3 --.

Signed and Sealed this

Twenty-sixth Day of October, 2004

JON W. DUDAS
*Director of the United States Patent and Trademark Office*